(12) United States Patent
Ras et al.

(10) Patent No.: US 12,347,099 B2
(45) Date of Patent: Jul. 1, 2025

(54) OBTAINING IMAGES FOR USE IN DETERMINING ONE OR MORE PROPERTIES OF SKIN OF A SUBJECT

(71) Applicant: KONINKLIJKE PHILIPS N.V., Eindhoven (NL)

(72) Inventors: Arnoldus Johannes Martinus Jozeph Ras, Mierlo (NL); Walter Hermans, Overpelt (BE); Willem Auke Westerhof, Drachten (NL); Babu Varghese, Eindhoven (NL); Willem Minkes, Emmeloord (NL); Sahil Wadhwa, Venlo (NL); Martijn Van Zutphen, Marum (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1030 days.

(21) Appl. No.: 16/970,657

(22) PCT Filed: Feb. 26, 2019

(86) PCT No.: PCT/EP2019/054721
§ 371 (c)(1),
(2) Date: Aug. 18, 2020

(87) PCT Pub. No.: WO2019/166428
PCT Pub. Date: Sep. 6, 2019

(65) Prior Publication Data
US 2020/0375466 A1    Dec. 3, 2020

(30) Foreign Application Priority Data
Feb. 27, 2018 (EP) ..................................... 18158913

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0077* (2013.01); *A61B 5/0531* (2013.01);
(Continued)

(58) Field of Classification Search
CPC ......... A61B 5/441; A61B 5/442; A61B 5/443; A61B 5/444; A61B 2562/04;
(Continued)

(56) References Cited

U.S. PATENT DOCUMENTS

| 7,151,956 B2 | 12/2006 | Satoh |
|---|---|---|
| 7,815,668 B2 | 10/2010 | Butler |

(Continued)

FOREIGN PATENT DOCUMENTS

| CN | 105640507 | 6/2016 |
|---|---|---|
| EP | 3384830 | 10/2018 |

(Continued)

OTHER PUBLICATIONS

International Search Report and Written Opinion Dated Jun. 21, 2019 for International Application No. PCT/EP2019/054721 Filed Feb. 26, 2019.

*Primary Examiner* — Charles A Marmor, II
*Assistant Examiner* — Andrew E Hoffpauir

(57) ABSTRACT

An apparatus for obtaining images for use in determining one or more properties of skin of a subject, the apparatus comprising an image sensor unit for generating an image of a skin sample, wherein the skin sample corresponds to an area of skin of the subject within a field of view, FOV, of the image sensor unit when the skin of the subject is spaced a predetermined working distance from the image sensor unit; a first light arrangement comprising one or more light sources for illuminating the skin of the subject; and a second light arrangement comprising one or more light sources for illuminating the skin of the subject. The one or more light (Continued)

sources in the first light arrangement are spaced from the image sensor unit and arranged such that light emitted by the light sources in the first light arrangement that is specularly reflected by a skin sample at the predetermined working distance is incident on the image sensor unit, and the one or more light sources in the second light arrangement are spaced from the image sensor unit and arranged such that light emitted by the light sources in the second light arrangement that is specularly reflected by a skin sample at the predetermined working distance is not incident on the image sensor unit.

22 Claims, 10 Drawing Sheets

(51) Int. Cl.
| | | |
|---|---|---|
| *A61B 5/0531* | (2021.01) | |
| *A61B 5/0537* | (2021.01) | |
| *A61B 5/103* | (2006.01) | |
| *H04N 23/56* | (2023.01) | |

(52) U.S. Cl.
CPC .......... *A61B 5/0537* (2013.01); *A61B 5/1032* (2013.01); *A61B 5/442* (2013.01); *A61B 5/443* (2013.01); *A61B 5/444* (2013.01); *H04N 23/56* (2023.01); *A61B 5/6898* (2013.01); *A61B 2562/0233* (2013.01); *A61B 2562/046* (2013.01); *A61B 2562/06* (2013.01); *A61B 2576/02* (2013.01); *G06T 2207/30088* (2013.01)

(58) Field of Classification Search
CPC . A61B 2562/06; A61B 5/0531; A61B 5/0537; A61B 5/0059; A61B 5/0077; G06T 2207/30088; G06T 7/0012
See application file for complete search history.

(56) References Cited

U.S. PATENT DOCUMENTS

| | | | |
|---|---|---|---|
| 2003/0063300 A1* | 4/2003 | Rubinstenn | H04N 23/61 |
| | | | 358/1.9 |
| 2004/0257439 A1 | 12/2004 | Shirai | |
| 2007/0035815 A1* | 2/2007 | Edgar | G06T 7/90 |
| | | | 359/359 |
| 2007/0073365 A1* | 3/2007 | Butler | A61N 5/0613 |
| | | | 607/88 |
| 2011/0301441 A1* | 12/2011 | Bandic | A61B 5/4875 |
| | | | 600/306 |
| 2012/0307028 A1 | 12/2012 | Kanamori | |
| 2013/0256605 A1 | 10/2013 | Gomi | |
| 2014/0055661 A1 | 2/2014 | Imamura | |
| 2015/0062380 A1 | 3/2015 | Nakamura | |
| 2015/0223749 A1* | 8/2015 | Park | G01N 21/6486 |
| | | | 600/476 |
| 2016/0270665 A1* | 9/2016 | Kantor | A61B 5/14546 |
| 2016/0278646 A1 | 9/2016 | Hu | |
| 2016/0296119 A1* | 10/2016 | Nakamura | A61B 5/0075 |
| 2019/0104980 A1* | 4/2019 | Farooq | A61B 5/0037 |
| 2020/0113441 A1 | 4/2020 | Varghese | |

FOREIGN PATENT DOCUMENTS

| | | |
|---|---|---|
| JP | 2005152258 | 6/2005 |
| JP | 2009213729 | 9/2009 |
| JP | 2011130808 | 7/2011 |
| KR | 20170023324 | 3/2017 |
| WO | 2008062967 | 5/2008 |
| WO | 2016076313 | 5/2016 |

* cited by examiner

OBTAINING IMAGES FOR USE IN DETERMINING ONE OR MORE PROPERTIES OF SKIN OF A SUBJECT

CROSS REFERENCE TO RELATED APPLICATIONS

This application is the U.S. National Phase application under 35 U.S.C. § 371 of International Application No. PCT/EP2019/054721 filed Feb. 26, 2019, published as WO 2019/166428 on Sep. 6, 2019, which claims the benefit of European Patent Application Number 18158913.6 filed Feb. 27, 2018. These applications are hereby incorporated by reference herein.

FIELD OF THE INVENTION

This disclosure relates to an apparatus for obtaining images for use in determining one or more properties of skin of a subject, and to a method and system for determining one or more properties of skin of a subject from images of a skin sample.

BACKGROUND OF THE INVENTION

In the skincare field, it is useful to determine properties of the skin of a subject. These properties can be used to adapt or personalise the operation of a personal care device, such as a shaver or skin cleansing device to the skin type of the subject, or be used to adapt a skin care routine to the skin type of the subject.

Although the subject could manually input their properties to a personal care device or skin care routine or coaching application (app), e.g. based on their personal knowledge of their skin, it is desirable to obtain objective measurements of these skin properties, preferably in an unobtrusive, or largely unobtrusive, way. As such, techniques have been developed for determining properties of the skin of a subject in which images of the skin of a subject are obtained, and the images analysed to determine values of the properties. Some of these techniques require the skin to be illuminated using one or more light sources, but the optimum arrangement of the light sources required to measure a particular skin property can differ from the optimum arrangement of light sources required for measuring a different skin property.

Therefore, there is a need for improvements in systems, apparatuses and methods for determining properties of skin of a subject.

SUMMARY OF THE INVENTION

According to a first specific aspect, there is provided an apparatus for obtaining images for use in determining one or more properties of skin of a subject, the apparatus comprising an image sensor unit for generating an image of a skin sample, wherein the skin sample corresponds to an area of skin of the subject within a field of view, FOV, of the image sensor unit when the skin of the subject is spaced a predetermined working distance from the image sensor unit; a first light arrangement comprising one or more light sources for illuminating the skin of the subject; and a second light arrangement comprising one or more light sources for illuminating the skin of the subject. The one or more light sources in the first light arrangement are spaced from the image sensor unit and arranged such that light emitted by the light sources in the first light arrangement that is specularly reflected by a skin sample at the predetermined working distance is incident on the image sensor unit; and the one or more light sources in the second light arrangement are spaced from the image sensor unit and arranged such that light emitted by the light sources in the second light arrangement that is specularly reflected by a skin sample at the predetermined working distance is not incident on the image sensor unit.

In some embodiments, the one or more light sources in the first light arrangement and the one or more light sources in the second light arrangement are arranged in a plane.

In some embodiments, the image sensor unit comprises an image sensor that is arranged in generally the same plane as the one or more light sources in the first light arrangement and the one or more light sources in the second light arrangement.

In some embodiments, the FOV of the image sensor unit is defined by one or more FOV angles, and wherein the one or more light sources in the first light arrangement are spaced from the image sensor unit in the direction of the plane by a distance that is equal to or less than $2*D*\tan(\theta_{min}/2)$ where D is the predetermined working distance, and $\theta_{min}$ is a smallest one of the one or more FOV angles.

In some embodiments, the FOV of the image sensor unit is defined by one or more FOV angles, and wherein the one or more light sources in the second light arrangement are spaced from the image sensor unit in the direction of the plane by a distance that is greater than $2*D*\tan(\theta_{max}/2)$ where D is the predetermined working distance, and $\theta_{max}$ is a largest one of the one or more FOV angles.

In some embodiments, each of the one or more light sources in the first light arrangement are spaced from the image sensor unit by a distance that is in the range of 3-7 millimetres.

In some embodiments, each of the one or more light sources in the second light arrangement are spaced from the image sensor unit by a distance that is in the range of 7-15 millimetres.

In some embodiments, the first light arrangement comprises a plurality of light sources. In some embodiments, the first light arrangement comprises at least three light sources arranged generally equidistant from the image sensor unit.

In some embodiments, the second light arrangement comprises a plurality of light sources. In some embodiments, the second light arrangement comprises at least three light sources arranged generally equidistant from the image sensor unit.

In some embodiments, the apparatus further comprises a first polarising filter arranged with respect to the image sensor unit such that the polarising filter polarises light incident on the image sensor unit. In these embodiments, the apparatus can further comprise a respective second polarising filter for each light source in the second light arrangement that is for polarising the light emitted by the light source in the second light arrangement, wherein a polarising direction of the second polarising filter is orthogonal to a polarising direction of the first polarising filter. In these embodiments, the apparatus can further comprise a third light arrangement comprising one or more light sources for illuminating the skin of the subject; wherein the one or more light sources in the third light arrangement are spaced from the image sensor unit and arranged such that light emitted by the light sources in the third light arrangement that is specularly reflected by a skin sample at the predetermined working distance is not incident on the image sensor unit. In these embodiments, the third light arrangement comprises a plurality of light sources. In these embodiments, the third light arrangement can comprise at least three light sources arranged generally in a ring around the image sensor unit. In these embodiments, each of the one or more light sources in the second light arrangement are spaced from the image sensor unit by a distance that is in the range of 7-11 millimetres, and each of the one or more light sources in the third light arrangement are spaced from the image sensor unit by a distance that is in the range of 11-15 millimetres.

According to a second aspect, there is provided a system for determining one or more properties of skin of a subject, the system comprising an apparatus according to the first aspect or any embodiment thereof; a control unit configured to receive images generated by the image sensor unit; and process the received images to determine one or more properties of the skin of the subject.

In some embodiments, the control unit is configured to process images generated by the image sensor unit when the one or more light sources in the first light arrangement are illuminating the skin of the subject to determine one or more first skin properties; and process images generated by the image sensor unit when the one or more light sources in the second light arrangement are illuminating the skin of the subject to determine one or more second skin properties.

In some embodiments, the control unit is further configured to selectively control the first light arrangement to illuminate the skin of the subject and to determine one or more first skin properties from a received image; and selectively control the second light arrangement to illuminate the skin of the subject and to determine one or more second skin properties from a received image.

In some embodiments, the one or more first skin properties are one or more of oiliness, gloss and skin texture.

In some embodiments, the one or more second skin properties are one or more of skin texture, colour, pigmentation, presence of spots and presence of hairs.

In some embodiments, the control unit is configured to process images generated by the image sensor when the one or more light sources in the third light arrangement are illuminating the skin of the subject to determine one or more third skin properties. In these embodiments, the one or more third skin properties includes skin texture.

In some embodiments, the control unit is further configured to output a signal representing the determined one or more properties of skin of the subject.

According to a third aspect, there is provided a method of determining one or more properties of skin of a subject, the method comprising illuminating the skin of the subject using a first light arrangement comprising one or more light sources; generating a first image of a skin sample using an image sensor unit when the first light arrangement is illuminating the skin of the subject, wherein the skin sample corresponds to an area of skin of the subject within a field of view, FOV, of the image sensor unit when the skin of the subject is spaced a predetermined working distance from the image sensor unit; illuminating the skin of the subject using a second light arrangement comprising one or more light sources; generating a second image of the skin sample using the image sensor unit when the second light arrangement is illuminating the skin of the subject; and processing the first image and second image using a control unit to determine one or more properties of the skin of the subject. The one or more light sources in the first light arrangement are spaced from the image sensor unit and arranged such that light emitted by the light sources in the first light arrangement that is specularly reflected by a skin sample at the predetermined working distance is incident on the image sensor unit, and the one or more light sources in the second light arrangement are spaced from the image sensor unit and arranged such that light emitted by the light sources in the second light arrangement that is specularly reflected by a skin sample at the predetermined working distance is not incident on the image sensor unit.

In some embodiments, the method comprises processing the first image to determine one or more first skin properties; and processing the second image to determine one or more second skin properties.

In some embodiments, the one or more first skin properties are one or more of oiliness, gloss and skin texture. In some embodiments, the one or more second skin properties are one or more of skin texture, colour, pigmentation, presence of spots and presence of hairs.

In some embodiments, the method further comprises the steps of illuminating the skin of the subject using a third light arrangement comprising one or more light sources; generating a third image of the skin sample using the image sensor unit when the third light arrangement is illuminating the skin of the subject, and processing the third image to determine one or more third skin properties. The one or more light sources in the third light arrangement are spaced from the image sensor unit and arranged such that light emitted by the light sources in the third light arrangement that is specularly reflected by a skin sample at the predetermined working distance is not incident on the image sensor unit. In these embodiments, the one or more third skin properties includes skin texture.

In some embodiments, the method further comprises the step of outputting a signal representing the determined one or more properties of skin of the subject.

According to a fourth aspect, there is provided a system for determining values of a plurality of properties of skin of a subject, the system comprising a control unit; and an apparatus for obtaining images for use in determining the values of the plurality of properties of skin of the subject. The apparatus comprises an image sensor unit for generating an image of a skin sample, wherein the skin sample corresponds to an area of skin of the subject within a field of view, FOV, of the image sensor unit when the skin of the subject is spaced a predetermined working distance from the image sensor unit; a first light arrangement comprising a plurality of light sources that are spatially distributed around an optical axis of the image sensor unit for illuminating the skin of the subject from a respective plurality of directions; a second light arrangement comprising one or more light sources for illuminating the skin of the subject. The plurality of light sources in the first light arrangement are spaced from the optical axis of the image sensor unit and arranged such that light emitted by the light sources in the first light arrangement that is specularly reflected by a skin sample at the predetermined working distance is incident on the image sensor unit; and the one or more light sources in the second light arrangement are spaced from the optical axis of the image sensor unit and arranged such that light emitted by the light sources in the second light arrangement that is specularly reflected by a skin sample at the predetermined working distance is not incident on the image sensor unit. The control unit is configured to selectively control each of the light sources in the first light arrangement to individually illuminate the skin of the subject; receive a respective plurality of first images from the image sensor unit, each first image being obtained by the image sensor unit when a respective light source in the first light arrangement is illuminating the skin; process each first image to determine a respective initial value for a first skin property and combine the determined initial values to determine a value for the first skin property; selectively control the second light arrangement to illuminate the skin of the subject; receive one or more second images generated by the image sensor unit, each second image being obtained by the image sensor unit when the second light arrangement is illuminating the skin of the subject; and process the one or more received second images to determine a value for one or more second skin properties.

In some embodiments, the plurality of light sources in the first light arrangement and the one or more light sources in the second light arrangement are arranged in a plane.

In some embodiments, the plurality of light sources in the first light arrangement and the one or more light sources in the second light arrangement are spaced from the skin of the subject by less than the predetermined working distance.

In some embodiments, the first light arrangement comprises at least three light sources arranged generally equidistant from the optical axis of the image sensor unit.

In some embodiments, the second light arrangement comprises a plurality of light sources. For example the second light arrangement can comprise at least three light sources arranged generally equidistant from the optical axis of the image sensor unit. In these embodiments, the control unit can be configured to selectively control the plurality of light sources in the second light arrangement to illuminate the skin of the subject at the same time.

In some embodiments, the first skin property is one of oiliness, gloss and skin texture. In embodiments where the first skin property is oiliness, the control unit can be configured to process each first image to determine a respective initial value for oiliness based on one or more parameters including an amount of specular reflection from the skin sample, a distribution, granularity and/or intensity of specular reflection from the skin sample, a roughness or texture of the skin, principal component analysis of the image, a histogram shape encoding of texture maps and contrast in the image.

In some embodiments, the second skin property is one of skin texture, colour, redness, pigmentation, pores, presence of spots and presence of hairs.

In alternative embodiments, the apparatus further comprises a first polarising filter arranged with respect to the image sensor unit such that the polarising filter polarises light incident on the image sensor unit. In these embodiments the apparatus can further comprise a respective second polarising filter for each light source in the second light arrangement that is for polarising the light emitted by the light source in the second light arrangement, wherein a polarising direction of the second polarising filter is orthogonal to a polarising direction of the first polarising filter. In these embodiments the second skin property can be one of colour, redness, spots and pigmentation. In these embodiments the apparatus can further comprise: a third light arrangement comprising one or more light sources for illuminating the skin of the subject; wherein the one or more light sources in the third light arrangement are spaced from the optical axis of the image sensor unit and arranged such that light emitted by the light sources in the third light arrangement that is specularly reflected by a skin sample at the predetermined working distance is not incident on the image sensor unit; wherein the control unit is further configured to: selectively control the third light arrangement to illuminate the skin of the subject; receive one or more third images generated by the image sensor unit, each third image being obtained by the image sensor unit when the third light arrangement is illuminating the skin of the subject; and process the one or more received third images to determine values for one or more third skin properties. In these embodiments the third light arrangement can comprise a plurality of light sources. In these embodiments the third light arrangement can comprise at least three light sources arranged generally equidistant from the optical axis of the image sensor unit. In these embodiments the control unit can be configured to selectively control the plurality of light sources in the third light arrangement to illuminate the skin of the subject at the same time. In these embodiments the third skin property can be one of pores and blackheads.

In some embodiments, the apparatus further comprises an impedance sensor for measuring an impedance of the skin of the subject; and the control unit is further configured to receive impedance measurements from the impedance sensor, and to process the received impedance measurements to determine a hydration level of the skin.

In some embodiments, the control unit is further configured to output a signal representing the determined value of the first skin property and/or the determined value of the second skin property.

In some embodiments, the control unit is comprised in the apparatus. In alternative embodiments, the control unit is separate from the apparatus.

According to a fifth aspect, there is provided a method of determining values of a plurality of properties of skin of a subject, the method comprising: illuminating the skin of the subject using a first light arrangement comprising a plurality of light sources, wherein the skin of the subject is illuminated individually by the plurality of light sources; generating a respective first image of a skin sample using an image sensor unit when each of the light sources in the first light arrangement is illuminating the skin of the subject, wherein the skin sample corresponds to an area of skin of the subject within a field of view, FOV, of the image sensor unit when the skin of the subject is spaced a predetermined working distance from the image sensor unit; illuminating the skin of the subject using a second light arrangement comprising one or more light sources; generating one or more second images of the skin sample using the image sensor unit when the second light arrangement is illuminating the skin of the subject; processing, using a control unit, each first image to determine a respective initial value for a first skin property and combining the determined initial values to determine a value for a first skin property; and processing, using the control unit, the one or more second images to determine a value for one or more second skin properties; wherein the plurality of light sources in the first light arrangement are spatially distributed around an optical axis of the image sensor unit to illuminate the skin of the subject from a plurality of directions, and the plurality of light sources are arranged such that light emitted by the light sources in the first light arrangement that is specularly reflected by a skin sample at the predetermined working distance is incident on the image sensor unit; wherein the one or more light sources in the second light arrangement are spaced from the optical axis of the image sensor unit and arranged such that light emitted by the light sources in the second light arrangement that is specularly reflected by a skin sample at the predetermined working distance is not incident on the image sensor unit.

Various embodiments of the methods according to the third and fifth aspects are also envisaged that correspond to the various embodiments of the apparatus and systems according to the first, second and fourth aspects.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF EMBODIMENTS

Figure 1:
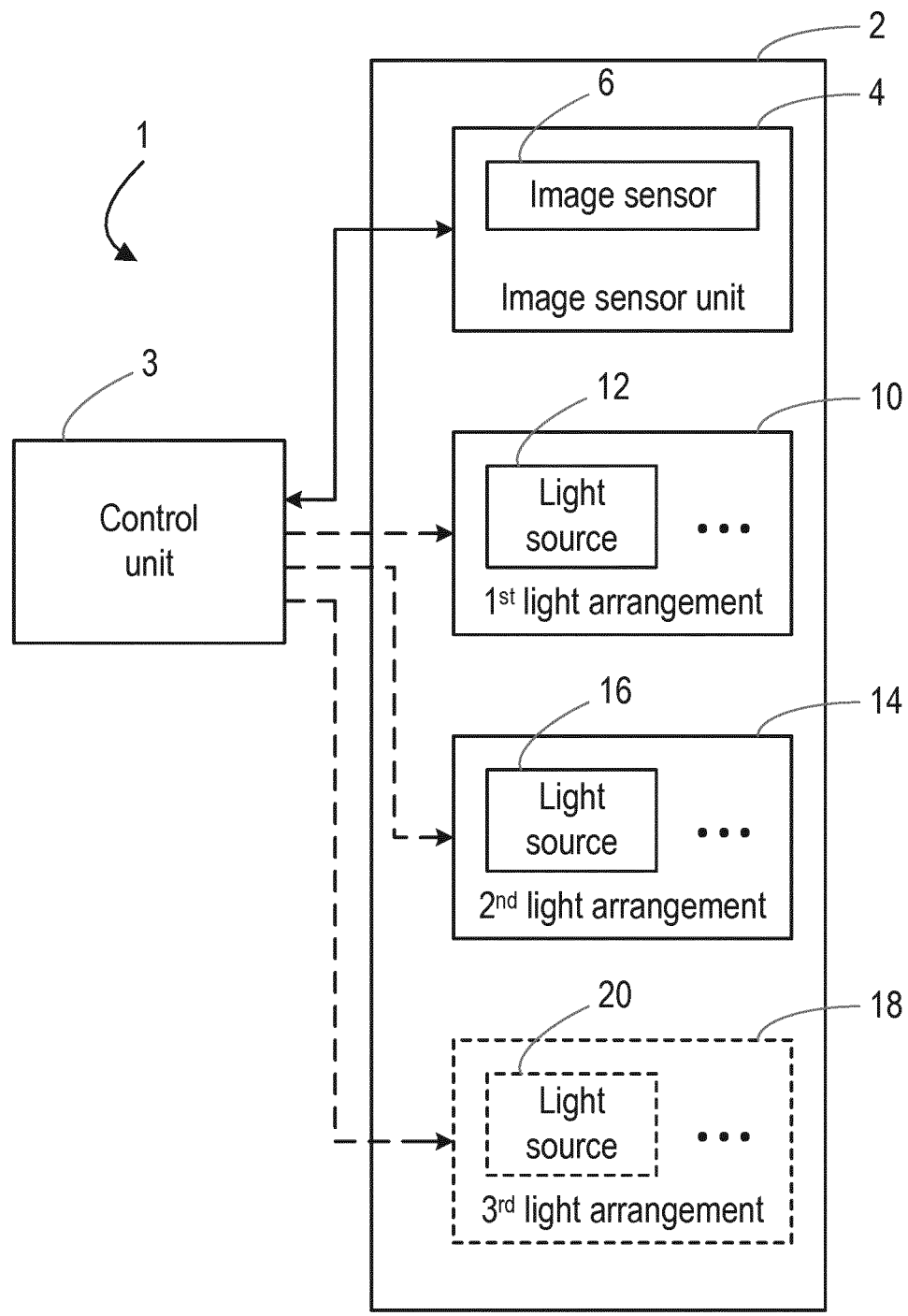
FIG. 1 is a block diagram of a system according to an exemplary aspect.

FIG. 1 is a block diagram of a system 1 according to an exemplary aspect. The system 1 is for determining one or more properties of skin of a subject, such as a human or animal. The skin properties that can be measured or determined by the system 1 can depend on the configuration of the system 1, as described in more detail below, but in general the system 1 can be configured to determine any one or more of skin properties such as oiliness, gloss, skin texture, colour, redness, pigmentation, pores, presence of spots (such as black heads and white heads) and presence of hairs.

The system 1 determines the skin properties by analysing images of the skin of the subject. The system 1 comprises an apparatus 2 for obtaining images of a skin sample and a control unit 3 for processing or analysing the images of the skin sample obtained by the apparatus 2 to determine one or more skin properties. Therefore, the apparatus 2 comprises an image sensor unit 4 that is for generating an image or a series of images of a skin sample. The image sensor unit 4 can comprise an image sensor 6 that responds to incident light to produce an image. The image sensor 6 may be, for example, a CCD (charged coupled device) based sensor, or a CMOS (complementary metal-oxide semiconductor) based sensor, similar to the types of image sensors used in digital cameras. Those skilled in the art will be aware of other types of image sensor that could be used. The image sensor 6 or image sensor unit 4 may be configured or capable of obtaining individual images of the skin of a subject, or a video sequence of the skin of a subject.

Although FIG. 1 only shows the image sensor unit 4 as comprising an image sensor 6, in various embodiments the image sensor unit 4 may comprise one or more additional components. For example, the image sensor unit 4 can comprise one or more lenses for focusing or otherwise influencing light that is incident on the image sensor 6 from the skin of a subject. In some embodiments, a polariser or polarising filter can be positioned in the light path from a skin sample to the image sensor 6 that acts to polarise light incident on the image sensor 6. This polariser or polarising filter is referred to herein as a first polariser or first polarising filter, and polarises light passing through the polariser or polarising filter in a first polarising direction. In some embodiments, the polariser or polarising plate is provided as part of the image sensor unit 4, but in other embodiments the polariser or polarising plate is separate from the image sensor unit 4.

Figure 2:
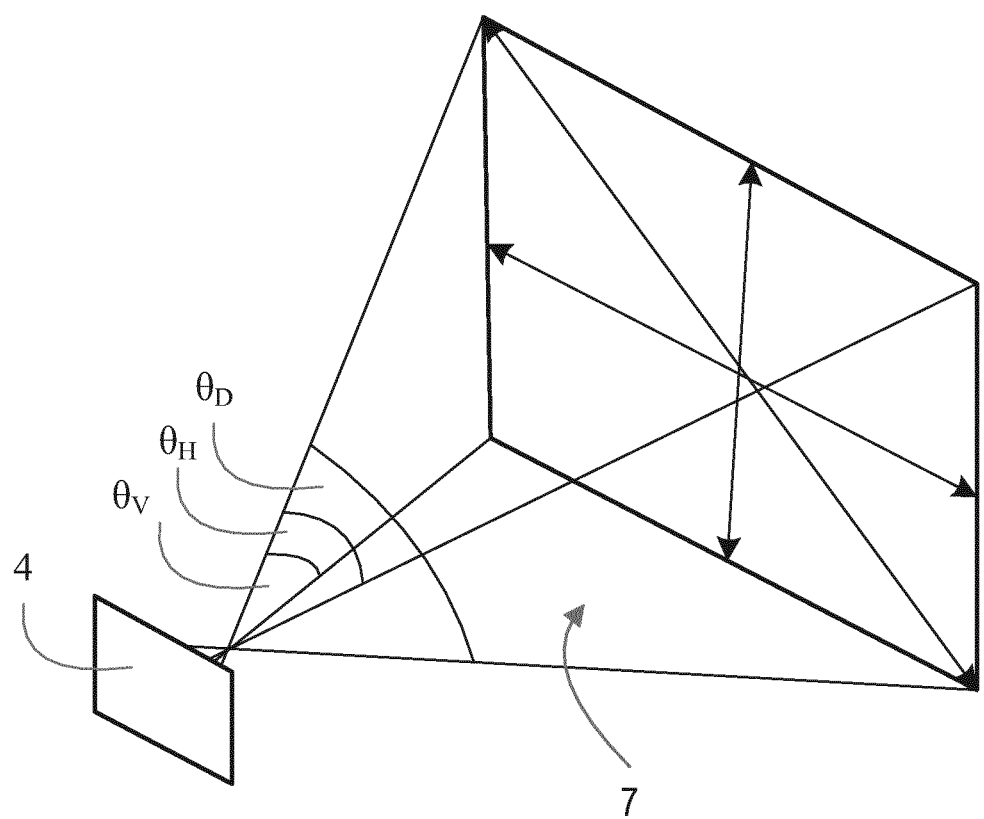
FIG. 2 illustrates the field of view of an image sensor unit.

The image sensor unit 4 has a field of view (FOV) defined by the range of angles of light that can be detected by the image sensor unit 4. The FOV of an exemplary image sensor unit 4 is illustrated in FIG. 2. Any light incident on the image sensor unit 4 from within the FOV region 7 can be received by the image sensor 6 and used to form an image. The FOV 7 can be characterised by two angles, a horizontal FOV angle, $\theta_H$, that is an angle measured in a horizontal plane (with respect to the image sensor 6) through which light can be detected by the image sensor unit 4, and a vertical FOV angle, $\theta_V$, that is an angle measured in a vertical plane (with respect to the image sensor 6) through which light can be detected by the image sensor unit 4. For an image sensor 6 that has a rectangular shape, i.e. as shown in FIG. 2, $\theta_H$ will be different to $\theta_V$ (and in FIG. 2 $\theta_H$ is greater than $\theta_V$, although this is merely an example). FIG. 2 shows a third angle $\theta_D$, which is the angle measured in a diagonal plane through which light can be detected by the image sensor unit 4. For a rectangular-shaped image sensor 6, the FOV in the diagonal plane ($\theta_D$) represents the maximum FOV angle of the image sensor unit 4. For the image sensor unit 4 shown in FIG. 2, the minimum FOV angle of the image sensor unit 4 is $\theta_V$.

It will be appreciated that the FOV of an image sensor unit 4 can be defined or controlled by optical components, such as lenses and apertures. As noted above, the image sensor unit 4 may comprise one or more lenses for focussing or otherwise influencing light that is incident towards the image sensor unit 4. In addition to one or more lenses, or alternatively, the image sensor unit 4 (or more generally the apparatus 2) can include an aperture plate that has an aperture of a defined size positioned in front of the image sensor unit 4 or image sensor 6 to restrict the field of view of the image sensor unit 4 or image sensor 6.

The control unit 3 is provided to process or analyse the images obtained or generated by the apparatus 2, and in some implementations the control unit 3 can control the operation of apparatus 2, for example controlling or commanding the apparatus 2 to obtain one or more images. The control unit 3 can be configured to execute or perform the methods described herein.

In some implementations, the control unit 3 can be part of the apparatus 2, i.e. the image sensor unit 4 and the control unit 3 can be part of the same device, for example a handheld device, that can be placed close to or on to skin of a subject. In this case, the control unit 3 can be connected or coupled to the apparatus 2 (and in particular the image sensor unit 4) in order to receive the images.

In other implementations, the control unit 3 can be in a separate device to the apparatus 2. For example, the apparatus 2 can be a handheld device that can be placed close to or on to the skin of a subject, and the control unit 3 can be part of a separate, second, device, for example a smartphone, tablet computer, laptop, desktop computer, server, etc. In the case of a smartphone or tablet computer, the control unit 3 may execute an application (app) in order to analyse the obtained images to determine the one or more skin properties. In these implementations, the system 1 can further comprise interface circuitry (not shown in FIG. 1) for enabling a data connection to and/or data exchange between the control unit 3 and the apparatus 2. The connection may be direct or indirect (e.g. via the Internet), and thus the interface circuitry can enable a connection between the apparatus 2 and control unit 3 via a network, such as the Internet, via any desirable wired or wireless communication protocol or protocols. For example, the interface circuitry can operate using WiFi, Bluetooth, Zigbee, or any cellular communication protocol (including but not limited to Global System for Mobile Communications (GSM), Universal Mobile Telecommunications System (UMTS), Long Term Evolution (LTE), LTE-Advanced, etc.). The control unit 3 and the apparatus 2 can have respective interface circuitry to enable a data connection or data exchange therebetween.

In either implementation (i.e. whether the control unit 3 is part of the apparatus 2 or separate from the apparatus 2), the apparatus 2 can be in the form of, or part of, a personal care device, such as (but not limited to) a shaver, a skin cleansing device or a skin treatment device.

In some embodiments (irrespective of whether the control unit 3 and the apparatus 2 are part of the same device), the system 1 can comprise interface circuitry for enabling a data connection or data exchange with other devices, including any one or more of servers, databases, and user devices. This interface circuitry can be used to communicate determined measurements of skin properties from the system 1 to another device, for example a server or data storage facility.

The control unit 3 can be implemented in numerous ways, with software and/or hardware, to perform the various functions described herein. The control unit 3 may comprise one or more microprocessors or digital signal processor (DSPs) that may be programmed using software or computer program code to perform the required functions and/or to control components of the control unit 3 to effect the required functions. The control unit 3 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), and field-programmable gate arrays (FPGAs).

The control unit 3 may comprise or be connected to a memory unit (not shown in FIG. 1) that can store data, information and/or signals for use by the control unit 3 in controlling the operation of the apparatus 2 and/or in executing or performing the methods described herein. In some implementations the memory unit stores computer-readable code that can be executed by the control unit 3 so that the control unit 3 performs one or more functions, including the methods described herein. The memory unit can comprise any type of non-transitory machine-readable medium, such as cache or system memory including volatile and non-volatile computer memory such as random access memory (RAM) static RAM (SRAM), dynamic RAM (DRAM), read-only memory (ROM), programmable ROM (PROM), erasable PROM (EPROM) and electrically erasable PROM (EEPROM), implemented in the form of a memory chip, an optical disk (such as a compact disc (CD), a digital versatile disc (DVD) or a Blu-Ray disc), a hard disk, a tape storage solution, or a solid state device, including a memory stick, a solid state drive (SSD), a memory card, etc.

To enable the image sensor unit 4 to obtain images of the skin of the subject and to enable the control unit 3 to process the images to determine one or more skin properties, the apparatus 2 further comprises a first light arrangement 10 that comprises one or more light sources 12 and a second light arrangement 14 that comprises one or more light sources 16. As described in more detail below, as different skin properties require different lighting or illumination conditions in order for the property to be determined by the control unit 3, the light source(s) 12 in the first light arrangement 10 and the light source(s) 16 in the second light arrangement 14 are spaced different distances from the image sensor unit 4 to provide appropriate lighting conditions for measuring respective skin properties. The spacing of the light sources 12, 16 is described in more detail below.

Each of the light source(s) 12 in the first light arrangement 10 and the light source(s) 16 in the second light arrangement 14 are for emitting light towards the skin of a subject when the apparatus 2 is placed on or close to a subject, thereby illuminating the skin of the subject. In particular, the first light arrangement 10 and second light arrangement 14 are for illuminating an area of skin of the subject within the field of view of the image sensor unit 4. Each of the light sources 12, 16 can be the same type of light source, or one or more of the light sources 12, 16 can be different from the other light sources 12, 16. A light source 12, 16 may be a light emitting diode (LED), a resonant cavity light emitting diode (RCLED), a vertical cavity surface emitting laser (VCSELs), an edge emitting laser, or any other suitable type of semiconductor light source. Alternatively or in addition, in some embodiments, a light source 12, 16 can be, for example, an organic light emitting diode (OLED), a passive-matrix OLED (PMOLED), an active-matrix OLED (AMOLED), or any other organic material based light source. Alternatively or in addition, in some embodiments, a light source 12, 16 can be, for example, a solid state light source. Those skilled in the art will be aware of other types of light source that could be used in the apparatus 2.

Although each of the first light arrangement 10 and the second light arrangement 14 may comprise one light source 12, 16, preferably each of the first light arrangement 10 and the second light arrangement 14 comprise a plurality of light sources 12, 16. In some embodiments, the first light arrangement 10 comprises two light sources 12, but in other embodiments the first light arrangement 10 comprises three, four, or more than four, light sources 12. In some embodiments, the second light arrangement 14 comprises two light sources 16, but in other embodiments the second light arrangement 14 comprises three, four, or more than four, light sources 16. In some embodiments, the first light arrangement 10 has the same number of light sources as the second light arrangement 14, but in other embodiments the first light arrangement 10 has a different number of light sources to the second light arrangement 14. Where the first light arrangement 10 and/or the second light arrangement 14 comprise multiple light sources 12, 16, the light sources 12, 16 in each arrangement may arranged around the image sensor unit 4 to provide uniform, or generally uniform, illumination to the skin. For example, the light sources 12, 16 for a particular arrangement 10, 14, may be provided in a ring around (e.g. equidistant or substantially equidistant from) the image sensor unit 4 to provide uniform illumination to the skin. Where a light arrangement comprises multiple light sources, the light sources in the arrangement may be configured to operate together, i.e. each of the light sources in the arrangement can emit light at the same time. That is, the control unit 3 can be configured to control the light sources in the arrangement so that they all emit light at the same time. Alternatively, the light sources in the arrangement may configured to operate sequentially or individually, i.e. each of the light sources in the arrangement can be controlled by the control unit 3 to emit light one at a time, with respective images being obtained when each of the light sources is emitting light. In some embodiments, a light arrangement may be controllable to switch between a mode in which all of the light sources are emitting light at the same time, and a mode in which the light sources emit light one at a time. That is, the control unit 3 can be configured to selectively operate the light sources in an arrangement in a first mode so that they all emit light at the same time and a second mode so that they emit light individually.

In some embodiments, the light sources 12, 16 in the first light arrangement 10 and the second light arrangement 14 are configured to emit white light. In some embodiments, any of the light sources 12, 16 in the first light arrangement 10 and the second light arrangement 14 can be configured to emit visible light, including but not limited to, white light, red light, green light and blue light. The colour of light emitted by the light sources 12, 16 in the first light arrangement 10 and the second light arrangement 14 may depend on the skin properties to be measured by the apparatus 2. In some embodiments, the light source(s) 12 in the first light arrangement 10 can be configured to emit visible light of any colour (including white light). In some embodiments, the light source(s) 16 in the second light arrangement 14 can be configured to emit visible light of any colour (including white light), ultraviolet (UV) light, and/or infrared (IR) light. In some embodiments, the colour of the light emitted by the light sources 12, 16 in the first light arrangement 10 and/or the second light arrangement 14 can be controllable, for example according to a particular skin property to be measured.

The light sources 12, 16 in the first light arrangement 10 and second light arrangement 14 can emit light that is unpolarised. In some embodiments, which can depend on the skin parameters to be measured by the apparatus 2, a polariser or polarising filter can be provided for each light source(s) 16 in the second light arrangement 14 that acts to polarise the light emit by the light source(s) 16 in the second light arrangement 14 before it is incident on the skin of the subject. These polariser(s) or polarising filter(s) are referred to herein as second polariser(s) or second polarising filter(s), and polarises light passing through the second polariser or second polarising filter in a second polarising direction. It will be appreciated that the second polariser(s) or second polarising filter(s) can be a separate component to the light source(s) 16 in the second light arrangement 14, or they can be integral to the light source(s) 16 in the second light arrangement 14. In some embodiments where polariser(s) or polarising filter(s) are provided for the light source(s) 16 in the second light arrangement 14, the light source(s) 12 in the first light arrangement 10 do not have polariser(s) or polarising filter(s).

In embodiments where a first polariser or first polarising filter is positioned in the light path from a skin sample to the image sensor unit 4, the first polarising filter and the second polarising filter(s) for the light source(s) in the second light arrangement 14 can be 'crossed' so that most of the light from the light source(s) in the second light arrangement 14 is not incident on the image sensor unit 4 (i.e. only light from the light source(s) in the second light arrangement 14 whose angle of polarisation is altered by reflection from the skin of the subject is able to pass through the first polarising filter and reach the image sensor unit 4/image sensor 6). Thus, the first polarising filter can be arranged so that the first polarising direction is orthogonal to the second polarising direction of the second polarising filter(s).

In some embodiments, the apparatus 2 can further comprise a third light arrangement 18 that comprises one or more light sources 20. The third light arrangement 18 can be provided for measuring other skin properties that cannot be measured (or that cannot be measured as reliably) using the light source(s) 12 in the first light arrangement 10 and the light source(s) 16 in the second light arrangement 14. In particular embodiments, the third light arrangement 18 is provided where the light from the second light arrangement 14 is polarised using the second polarisers or second polarising filters. In these embodiments, the light source(s) 20 in the third light arrangement 18 do not have polariser(s) or polarising filter(s).

Similar to the first light arrangement 10 and the second light arrangement 14, each of the light source(s) 20 in the third light arrangement 18 are for emitting light towards the skin of a subject when the apparatus 2 is placed on or close to a subject, thereby illuminating the skin of the subject. In particular, the third light arrangement 18 is for illuminating an area of skin of the subject within the field of view of the image sensor unit 4. The light source(s) 20 can be the same type of light source as the light sources 12, 16 in the first light arrangement 10 and the second light arrangement 14, or the light sources 20 can be different to the other light sources 12, 16. A light source 20 may be a LED, a RCLED, a VCSEL, an edge emitting laser, or any other suitable type of semiconductor light source. Alternatively or in addition, in some embodiments, a light source 20 can be, for example, an OLED, a PMOLED, an AMOLED, or any other organic material based light source. Alternatively or in addition, in some embodiments, a light source 20 can be, for example, a solid state light source. Those skilled in the art will be aware of other types of light source that could be used in the apparatus 2.

Although the third light arrangement 18 may comprise one light source 20, preferably the third light arrangement 18 comprises a plurality of light sources 20. In some embodiments, the third light arrangement 18 comprises two light sources 20, but in other embodiments the third light arrangement 18 comprises three, four, or more than four, light sources 20. In some embodiments, the third light arrangement 18 has the same number of light sources as the first light arrangement 10 and/or the second light arrangement 14, but in other embodiments the third light arrangement 18 has a different number of light sources to the first light arrangement 10 and the second light arrangement 14. Where the third light arrangement 18 comprises multiple light sources 20, the light sources 20 in each arrangement may arranged around the image sensor unit 4 to provide uniform, or generally uniform, illumination to the skin. For example, the light sources 20 may be provided in a ring around (e.g. equidistant from or substantially equidistant from) the image sensor unit 4 to provide uniform illumination to the skin. As noted above with respect to the first light arrangement 10 and the second light arrangement 14, the control unit 3 may be configured to control the light sources 20 in the third light arrangement 18 so that they emit light at the same time, and/or control the light sources 20 in the third light arrangement 18 so that they emit light sequentially or individually.

In some embodiments, the light source(s) 20 in the third light arrangement 18 are configured to emit white light. In some embodiments, any of the light source(s) 20 in the third light arrangement 18 can be configured to emit visible light, including but not limited to, white light, red light, green light and blue light. The colour of light emitted by the light source(s) 20 in the third light arrangement 18 may depend on the skin properties to be measured by the apparatus 2. In some embodiments, the light source(s) 20 in the third light arrangement 18 can be configured to emit visible light of any colour (including white light), infrared (IR) light, and/or ultraviolet (UV) light.

The first light arrangement 10, the second light arrangement 14 and (if present) the third light arrangement 18 can be controlled by the control unit 3. For example, the control unit 3 can control the activation or deactivation of a particular light arrangement or particular light source(s) in a light arrangement according to a particular skin property to be measured.

In some embodiments, the apparatus 2 can comprise a user interface (not shown in FIG. 1) that includes one or more components that enables a user of apparatus 2 (e.g. the subject) to input information, data and/or commands into the apparatus 2, and/or enables the apparatus 2 to output information or data to the user of the apparatus 2. The user interface can comprise any suitable input component(s), including but not limited to a keyboard, keypad, one or more buttons, switches or dials, a mouse, a track pad, a touchscreen, a stylus, a camera, a microphone, etc., and the user interface can comprise any suitable output component(s), including but not limited to a display screen, one or more lights or light elements, one or more loudspeakers, a vibrating element, etc.

In some further embodiments, the apparatus 2 can also determine a skin property such as hydration level, and the apparatus 2 can further comprise an impedance sensor for measuring the impedance of the skin. The impedance sensor may be positioned so that it measures the impedance of a part of the skin that is different to the skin sample, e.g. skin that is adjacent to the skin sample. The impedance sensor can comprise two or more electrodes that are to be placed in contact with the skin, with the impedance being measured by applying a current to the skin through the electrodes.

It will be appreciated that a practical implementation of an apparatus 2 may include additional components to those shown in FIG. 1. For example the apparatus 2 may also include a power supply, such as a battery, or components for enabling the apparatus 2 to be connected to a mains power supply.

As noted above, different skin properties require different lighting conditions in order for the property to be determined by the control unit 3 from an acquired image, and so the light source(s) 12 in the first light arrangement 10, the light source(s) 16 in the second light arrangement 14 and the light source(s) 20 in the third light arrangement 18 (if present) are spaced different distances from the image sensor unit 4 to provide appropriate lighting conditions for measuring respective skin properties. In particular, to measure some skin properties, such as gloss and oiliness, it is desirable for light to be specularly reflected from the skin sample towards the image sensor unit 4 so that the acquired image shows a bright spot (or 'hotspot'). Skin texture can also be measured using an image acquired when light is specularly reflected from the skin sample towards the image sensor unit 4. For other skin properties, such as the skin colour, redness, skin pigmentation, pores, the presence of spots (such as black heads and white heads) and the presence of hairs, it is desirable for the acquired image to be generated using diffuse light, and so light should not be specularly reflected from the skin sample towards the image sensor unit 4 (and therefore the acquired image will not show a bright spot or 'hotspot' corresponding to the light source). Skin texture can also be measured using an image acquired using diffuse light. Preferably, in obtaining images for measuring skin colour, redness, skin pigmentation, the presence of spots (such as black heads and white heads) and/or the presence of hairs, the light incident on the skin should be polarised, and the apparatus 2 should include the first polariser arranged orthogonally to the polarisation of the light incident on the skin.

Therefore, embodiments provide that the light source(s) 12 in the first light arrangement 10 are arranged with respect to the image sensor unit 4 so that light emitted by the light source(s) 12 in the first light arrangement 10 towards a skin sample at some predetermined or desired working distance from the image sensor unit 4 is specularly reflected by the skin sample and incident on the image sensor unit 4. Thus, specular reflection(s) will be visible in the image or images obtained by the image sensor unit 4. In this way, an image or images acquired when the first light arrangement 10 is used to illuminate the skin sample can be processed or analysed by the control unit 3 to determine skin properties such as gloss, oiliness and texture. Embodiments also provide that the light source(s) in the second light arrangement 14 are arranged with respect to the image sensor unit 4 so that light emitted by the light source(s) 16 in the second light arrangement 14 towards the skin sample at the predetermined or desired working distance from the image sensor unit 4 that is specularly reflected by the skin sample is not incident on the image sensor unit 4. Thus, specular reflection(s) will not be visible in the image or images obtained by the image sensor unit 4. In this way, an image or images acquired when the second light arrangement 14 is used to illuminate the skin sample can be processed or analysed by the control unit 3 to determine skin properties such as skin colour, redness, skin pigmentation, the presence of spots (such as black heads and white heads), the presence of hairs and skin texture.

Figure 3:
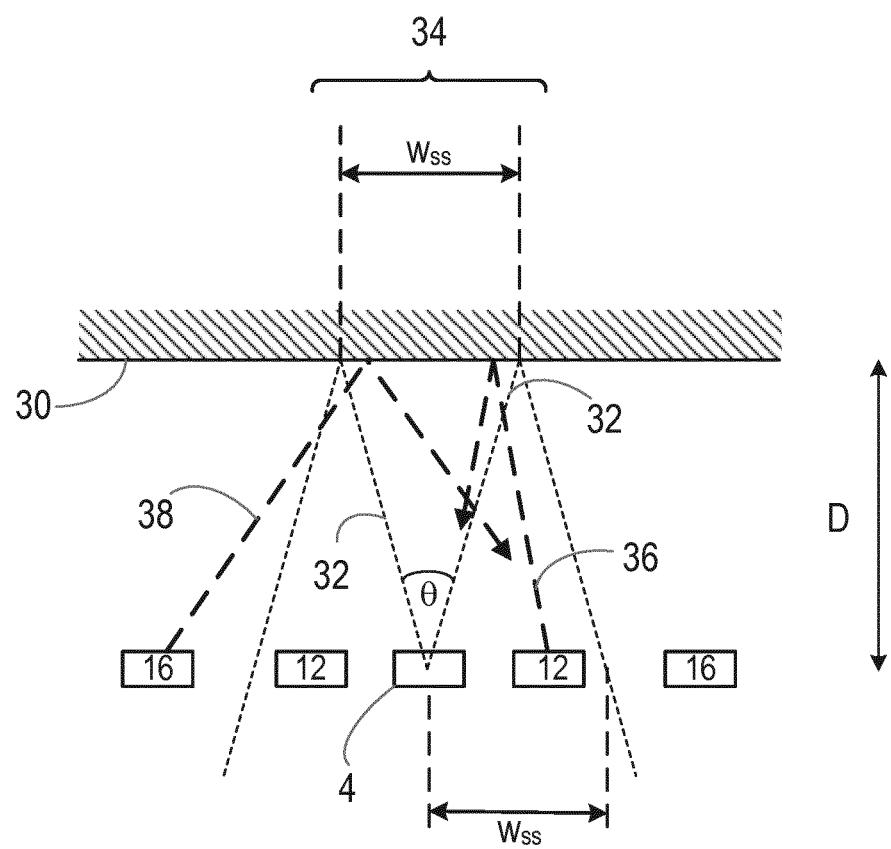
FIG. 3 shows a cross-section through an apparatus according to an embodiment.

A cross-section through an apparatus 2 is shown in FIG. 3 to illustrate an exemplary arrangement of the first light arrangement 10 and second light arrangement 14 with respect to an image sensor unit 4 according to various embodiments. In this exemplary arrangement, the first light arrangement 10, second light arrangement 14 and the image sensor unit 4 are in generally the same plane. FIG. 3 shows an apparatus 2 placed close to the skin 30 of a subject, and in particular the apparatus 2 is placed close to the skin 30 of the subject so that the image sensor unit 4 and the light source(s) 12, 16 of the first light arrangement 10 and the second light arrangement 14 are spaced from the skin 30 by a working distance D. Although not shown in FIG. 3, the apparatus 2 may be shaped or configured so that the image sensor unit 4 and the light source(s) 12, 16 of the first light arrangement 10 and the second light arrangement 14 can be reliably spaced from the skin 30 by the working distance D. For example, the apparatus 2 may comprise a spacer that is on or part of a housing of the apparatus 2, that extends beyond the image sensor unit 4, the first light arrangement 10 and the second light arrangement 14 so that the spacer can be placed in contact with the skin 30, thereby spacing the components 4, 10, 14 the distance D from the skin 30. In some embodiments, the working distance D can be between 20 millimetres (mm) and 80 mm, although those skilled in the art will appreciate that the working distance D may be less than 20 mm or greater than 80 mm.

As described above, the image sensor unit 4 has a field of view 7 defined by one or more angles, and in FIG. 3 this angle is simply denoted angle $\theta$. It will be appreciated that depending on the specific cross-section through the apparatus 2 that FIG. 3 represents, the angle θ may correspond to any of the angles between $θ_V$ and $θ_D$ in FIG. 2 (inclusive), noting that the vertical FOV angle $θ_V$ is the smallest FOV angle in FIG. 2 and the diagonal FOV angle $θ_D$ is the largest FOV angle in FIG. 2. The boundary of the FOV 7 of the image sensor unit 4 is shown by dashed lines 32. When the apparatus 2 is positioned close to the skin 30, the FOV 7 of the image sensor unit 4 is able to acquire images of a part of the skin 30, and this is shown as skin sample 34. Thus, as used herein, the term 'skin sample' refers to an area of skin 30 of the subject within the FOV of the image sensor unit 4 when the skin 30 is spaced the predetermined working distance D from the image sensor unit 4. In FIG. 3 the skin sample 34 has a width denoted $w_{ss}$, which is given by $2*D*\tan(θ/2)$.

Two light sources 12 for the first light arrangement 10 are shown in FIG. 3. The light sources 12 are spaced from the image sensor unit 4 (as measured in a plane that is parallel to the plane of the skin sample 34) by a distance that is equal to or less than the width $w_{ss}$ of the skin sample 34. In this way, as the light sources 12 and the image sensor 4 are in the same plane, light emitted by these light sources 12 can be specularly reflected by the skin sample 30 towards the image sensor unit 4, and the image sensor unit 4 can produce an image from this specularly reflected light. An exemplary light ray 36 from one of the light sources 12 being specularly reflected by the skin sample 34 towards the image sensor unit 4 is shown in FIG. 3.

Two light sources 16 for the second light arrangement 14 are also shown in FIG. 3. The light sources 16 are spaced from the image sensor unit 4 (as measured in the plane that is parallel to the plane of the skin sample 34) by a distance that is more than the width $w_{ss}$ of the skin sample 34. In this way, as the light sources 16 and the image sensor 4 are in the same plane, light emitted by these light sources 16 that is specularly reflected by the skin sample 34 will not be incident on the image sensor unit 4. Instead, only diffuse light provided by the light sources 16 will be incident on the image sensor unit 4 and contribute to an image of the skin sample 34. An exemplary light ray 38 from one of the light sources 16 being specularly reflected by the skin sample 34 away from the image sensor unit 4 is shown in FIG. 3. It will be appreciated that by definition of the FOV 7 of the image sensor unit 4, any light from the light sources 16 that is specularly reflected by skin 30 that is not part of skin sample 34 cannot be detected by the image sensor unit 4.

In embodiments where a third light arrangement 18 is provided, similar to the second light arrangement 14, the light source(s) 20 forming the third light arrangement 18 can be spaced from the image sensor unit 4 (as measured in the plane that is parallel to the plane of the skin sample 34) by a distance that is more than the width $w_{ss}$ of the skin sample 34. In some embodiments, the light source(s) 20 forming the third light arrangement 18 can be spaced from the image sensor unit 4 by a similar distance to the light source(s) 16 forming the second light arrangement 14. In other embodiments, the light source(s) 20 forming the third light arrangement 18 can be spaced from the image sensor unit 4 by a greater distance than the light source(s) 16 forming the second light arrangement 14. In other embodiments, the light source(s) 20 forming the third light arrangement 18 can be spaced from the image sensor unit 4 by a smaller distance than the light source(s) 16 forming the second light arrangement 14 (although still greater than $w_{ss}$).

It will be appreciated that the exemplary spacing of the light sources 12, 16 described above is based on the light sources 12, 16 being in the same plane as each other, and in the same plane as the image sensor unit 4. If the light sources 12, 16 are in a different plane to the image sensor unit 4 (for example if the light sources 12, 16 are a distance from the skin 30 that is different to the distance from the image sensor unit 4 to the skin 30), then the requirements on the distance between the light sources 12, 16 and the image sensor unit 4 will need to be adjusted accordingly in order to provide that light from the first light arrangement 10 is specularly reflected by the skin sample 34 to the image sensor unit 4 and light from the second light arrangement 14 that is specularly reflected by the skin sample 34 is not incident on the image sensor unit 4. An exemplary embodiment where the light arrangements are positioned between the skin 30 and the image sensor unit 4 is described below with reference to FIGS. 8 and 9.

Figure 4:
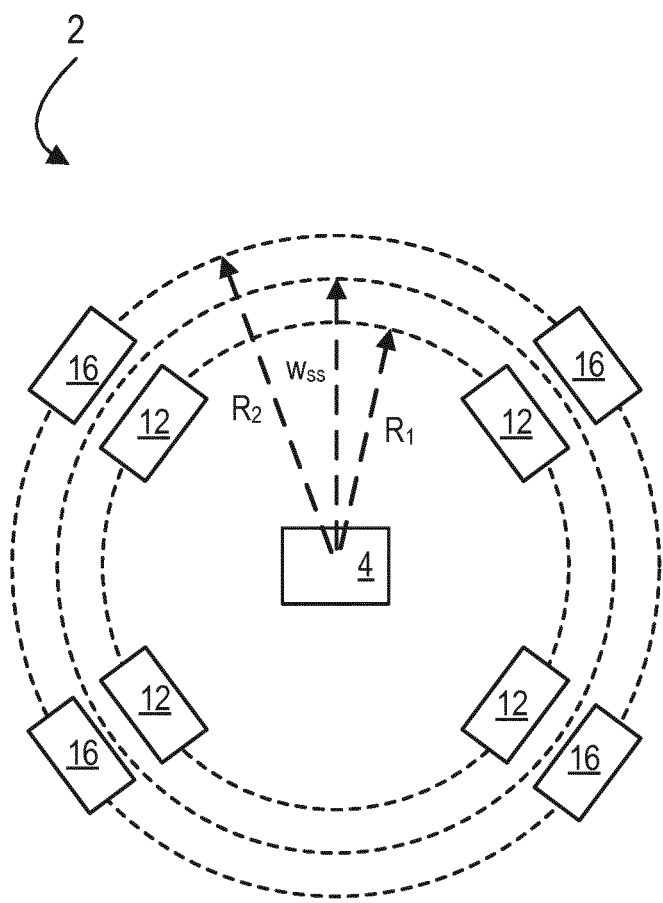
FIG. 4 is a front view of an apparatus showing an exemplary arrangement of light sources according to an embodiment.

FIG. 4 shows a front view of an exemplary apparatus 2. In this exemplary apparatus 2, the light sources and the image sensor 4 are in the same plane, or generally in the same plane. Thus, FIG. 4 shows the apparatus 2 from the point of view of the skin sample 34. In FIG. 4 each of the first light arrangement 10 and the second light arrangement 14 comprise four light sources 12, 16 that are arranged in respective rings around the image sensor unit 4, with the light sources 12, 16 each being offset diagonally with respect to the image sensor unit 4. Thus the light sources 12, 16 in each ring are spatially distributed around the optical axis of the image sensor unit 4 (i.e. an axis that extends perpendicularly from the centre of the plane of the image sensor unit 4), so that the skin 30 is illuminated from different directions. The light sources 12, 16 in each ring are generally evenly spaced with respect to each other around the image sensor unit 4, although other configurations are possible. The light sources 12 in the first light arrangement 10 are each spaced from the image sensor unit 4 (and specifically spaced from the optical axis of the image sensor unit 4) by a distance $R_1$ that is equal to or less than $w_{ss}$ (which in this exemplary arrangement is the width of the diagonal dimension of the FOV 7 since the light sources 12, 16 in both arrangements are offset diagonally from the image sensor unit 4), and the light sources 16 in the second light arrangement 14 are each spaced from the image sensor unit 4 (and specifically spaced from the optical axis of the image sensor unit 4) by a distance $R_2$ that is greater than $w_{ss}$. It will be appreciated that although each of the four light sources 12 of the first light arrangement 10 are aligned in a radial direction with a respective one of the four light sources 16 of the second light arrangement 14, this is purely exemplary, and other configurations are possible.

Figure 5:
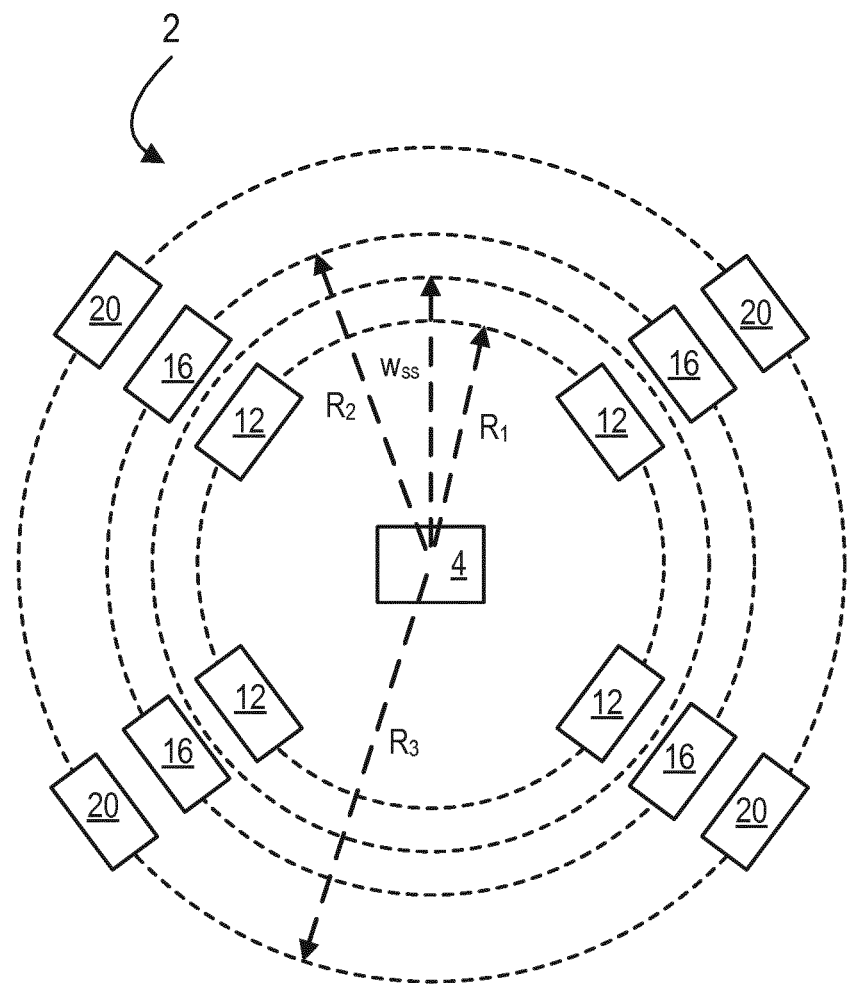
FIG. 5 is a front view of an apparatus showing another exemplary arrangement of light sources according to an embodiment.

FIG. 5 shows a front view of another exemplary apparatus 2. In this exemplary apparatus 2, the light sources and the image sensor 4 are again in the same plane, or generally in the same plane. The apparatus 2 in FIG. 5 corresponds to the apparatus 2 in FIG. 4, with the addition of a third light arrangement 18 comprising four light sources 20, with each light source 20 being offset diagonally from the image sensor unit 4. Again the light sources 20 are spatially distributed around the optical axis of the image sensor unit 4 so that the skin 30 is illuminated from different directions. In this exemplary apparatus 2, a first polariser is provided to polarise the light incident on the image sensor unit 4, and each of the four light sources 16 in the second light arrangement 14 have respective second polarisers (that are arranged orthogonally to the first polariser). The light emitted by the light sources 12 in the first light arrangement 10 and the light sources 20 in the third light arrangement 18 is unpolarised. In FIG. 5, the third light arrangement 18 is arranged in a respective ring around the image sensor unit 4, with the light sources 20 in the third light arrangement 18 being generally evenly spaced with respect to each other around the image sensor unit 4, and being spaced from the image sensor unit 4 (and specifically spaced from the optical axis of the image sensor unit 4) by a distance $R_3$ that is greater than $R_2$ (and therefore greater than $w_{ss}$). The light sources 20 in the third light arrangement 18 are each aligned in a radial direction with a respective one of the four light sources 12, 16 of the first light arrangement 10 and the second light arrangement 14, but it will be appreciated that this is purely exemplary, and other configurations are possible.

In some embodiments, the distance $R_1$ between the light sources 12 of the first light arrangement 10 is at least 4 millimetres (mm), or another distance in the range of 3-7 mm. In some embodiments, the distance $R_2$ between the light sources 16 of the second light arrangement 14 is at least 8 mm, or another distance in the range of 7-15 mm. In some embodiments, the distance $R_3$ between the light sources 20 of the third light arrangement 18 is at least 8 mm, or another distance in the range of 7-15 mm. In some embodiments, the distance $R_2$ between the light sources 16 of the second light arrangement 14 is at least 8 mm, or another distance in the range of 7-11 mm and the distance $R_3$ between the light sources 20 of the third light arrangement 18 is at least 12 mm, or another distance in the range of 11-15 mm.

In a specific implementation where the working distance D is 60 mm and the field of view of the image sensor unit 4 defines a skin sample 34 that has dimensions of 12 mm*9 mm, the light sources 12 of the first light arrangement 10 should be less than 9 mm from the image sensor unit 4, and this provides an angle of incidence of the light from the first light arrangement 10 from the skin sample 34 on to the image sensor unit 4 (as measured with respect to an optical axis of the image sensor unit 4) of no more than 8.5° (based on the smallest dimension of the field of view of 9 mm), and in a particular embodiment the light sources 12 of the first light arrangement 10 are spaced from the image sensor unit 4 to provide an angle of incidence of light of 5.5°. The angle of incidence should therefore be at least 8.5° for light emitted by the light source(s) 16 in the second light arrangement 14 and/or the light source(s) 20 in the third light arrangement 18 (where those light sources 16 are offset with respect to the shortest dimension of the image sensor unit 4) and at least 14 for light emitted by the light source(s) 16 in the second light arrangement 14 and/or the light source(s) 20 in the third light arrangement 18 if those light sources are offset diagonally from the image sensor 6 (given that the largest dimension of the field of view is 15 mm—the length from corner to corner of the skin sample 34 in the FOV).

In another specific implementation where the working distance D is 20 mm and the field of view of the image sensor unit 4 defines a skin sample 34 that has dimensions of 10 mm*7.5 mm, the light sources 12 of the first light arrangement 10 should be less than 7.5 mm from the image sensor unit 4, and this provides an angle of incidence of the light from the first light arrangement 10 from the skin sample 34 on to the image sensor unit 4 (as measured with respect to an optical axis of the image sensor unit 4) of no more than 20 (based on the smallest dimension of the field of view of 7.5 mm). The angle of incidence should therefore be at least 200 for light emitted by the light source(s) 16 in the second light arrangement 14 and/or the light source(s) 20 in the third light arrangement 18 (where those light sources 16, 20 are offset with respect to the shortest dimension of the image sensor unit 4) and at least 32° for light emitted by the light source(s) 16 in the second light arrangement 14 and/or the light source(s) 20 in the third light arrangement 18 if those light sources are offset diagonally from the image sensor 6 (given that the largest dimension of the field of view is 12.5 mm—the length from corner to corner of the skin sample 34 in the FOV).

Generally, the light source(s) 12 in the first light arrangement 10 are spaced from the image sensor unit 6 by a distance that is equal to or less than $$2*D*\tan(\theta_{min}/2)$$

where D is the predetermined working distance, and $\theta_{min}$ is a smallest FOV angle of the image sensor unit 4. In the example shown in FIG. 2 $\theta_{min}$ is $\theta_V$. It will be appreciated that this applies regardless of the position of a light source(s) 12 around the image sensor unit 4 (since it uses the smallest FOV angle). However, if the light source(s) 12 in the first light arrangement 10 are only positioned with respect to longest dimension of the FOV of the image sensor unit 4 (e.g. diagonally, as shown in FIGS. 4 and 5), then $\theta_{min}$ can be substituted for $\theta_D$ to determine the maximum spacing of the light source(s) 12 in the first light arrangement 10 from the image sensor unit 4.

In addition, the light source(s) 16 in the second light arrangement 14 and light source(s) 20 in the third light arrangement 18 are spaced from the image sensor unit 4 by a distance that is greater than:

$$2*D*\tan(\theta_{max}/2)$$

where D is the predetermined working distance, and $\theta_{max}$ is a largest FOV angle of the image sensor unit 4. In the example shown in FIG. 2 $\theta_{max}$ is $\theta_D$. It will be appreciated that this applies regardless of the position of the light source(s) 16, 20 around the image sensor unit 4 (since it uses the largest FOV angle). However, if the light source(s) 16, 20 in the second light arrangement 14 and the third light arrangement 18 are only positioned with respect to a shorter dimension of the FOV of the image sensor unit 4 (e.g. vertically or horizontally in the case an image sensor unit 4 oriented as shown in FIG. 2), then $\theta_{msx}$ can be substituted for $\theta_V$ in the case of vertical position or $\theta_H$ in the case of horizontal position to determine the minimum spacing of the light source(s) 16 in the second light arrangement 14 and the light source(s) 20 in the third light arrangement 18 from the image sensor unit 4.

As noted above, the lighting or illumination conditions required to measure a particular skin property varies depending on the skin property itself. These lighting or illumination conditions include whether there is specular reflection from the relevant light arrangement 10, 14, 18 in the FOV 7 of the image sensor unit 4, the polarisation of light incident on the image sensor unit 4 and the colour of the emitted light. The conditions can also relate to the light source-image sensor distance, the angle of incidence, the emitted light divergence angle, the polarisation of the light incident on the image sensor 6, the number of light sources, the homogeneity of illumination, whether there should be hotspots (specular reflection) in the field of view of the image sensor unit 4, whether the light sources should be operated sequentially (individually) or simultaneously, etc. For instance, for measuring skin oiliness or gloss, light that is specularly reflected from the skin sample 34 to the image sensor unit 4 has to be within the field of view 7 of the image sensor unit 4 and multiple light sources have to be sequentially or individually enabled or activated to average out the effect of shadowing resulting from illuminating the skin sample 34 from different angles/directions (i.e. from different spatial locations). However, the optimal illumination conditions for measuring skin colour, redness or spots (where spots are identified by their colour) require polarised light and homogenous illumination, and specular hot spots must not be in the FOV 7.

By providing multiple light arrangements 10, 14 in separate positions with respect to the field of view of the image sensor unit 6, it is possible to realise the right illumination conditions for measuring different types of skin parameters within a single apparatus 2.

Table 1 below summarises several lighting or illumination conditions that can be used to measure various different skin properties. It will be appreciated that the information contained in Table 1 is merely exemplary, and variations to one or more of the lighting or illumination conditions is possible.

TABLE 1

| Skin property | Light arrangement to use | Parallel or sequential (individual) | Polarisation (S = image sensor; L = light sources) | Light source divergence | RGB detector channel |
|---|---|---|---|---|---|
| Oiliness | $1^{st}$ | Sequential | S | Wide | RGB |
| Gloss | $1^{st}$ | Sequential | S | Wide | RGB |
| Texture | $1^{st}$ or $3^{rd}$ | Sequential | S | Narrow | B or G |
| Texture | $2^{nd}$ | Sequential | S + L | Narrow | B or G |
| Colour | $2^{nd}$ | Parallel | S + L | Wide | RGB |
| Redness | $2^{nd}$ | Parallel | S + L | Wide | RGB |
| Pores/blackheads | $3^{rd}$ | Parallel | S | Wide | RGB |
| Pigmentation | $2^{nd}$ | Parallel | S + L | Wide | RGB |
| Spots | $2^{nd}$ | Parallel | S + L | Wide | RGB |
| Hairs | $2^{nd}$ | Parallel | S + L | Wide | RGB |

In Table 1, parallel or sequential refers to whether the light sources in a light arrangement should be operated together (i.e. parallel) or one at a time (i.e. sequentially or individually). In the latter case, multiple images (or a video sequence) may be required to reliably determine the skin parameter, with each of the multiple images being obtained when a different one of the light sources in the light arrangement is being operated. As skin is anisotropic, reflections from the skin can differ based on the position of the light source relative to the image sensor unit 4, and so a measure for the skin property (e.g. gloss or oiliness) is preferably derived from an average of the multiple images (although a single image obtained using a single light source 12 can be used if desired). The use of multiple images provides a more stable value for the skin property, and is less susceptible to the orientation of the apparatus 2 on the skin, which can help provide consistency between successive measurements of the skin property, without sacrificing sensitivity of the measurement. Thus, the control unit 3 can selectively control each of the light sources 12 in the first light arrangement 10 to individually illuminate the skin of the subject, and the image sensor unit 4 can acquire a respective image when each of the light sources 12 is active. The control unit 3 can process each of these images to determine a respective initial value for a skin property (e.g. gloss, oiliness, shine and/or texture), and then combine the initial values (e.g. by averaging, such as the mean, mode or median) to determine a value for the skin property.

In some embodiments, shine can be determined as the amount (e.g. intensity) of specular reflection from the skin sample 34. The skin parameter oiliness can represent how oily the skin sample appears, and is influenced by the shine of the skin, the sweatiness of the skin, and the amount of sebum on the skin. Oiliness can be determined from each image based on one or more parameters, including the amount (e.g. intensity) of reflection, the distribution, granularity and/or intensity of specular reflection from the skin sample 34, a roughness or texture of the skin, principal component analysis of the image, a histogram shape encoding of texture maps, and contrast in the image.

The polarisation column indicates whether a polariser is required at a light source (L), at the image sensor unit 4 (S) or both (S+L). The light source divergence (otherwise referred to as the level of collimation of the emitted light) indicates the desired divergence of the light source used to measure the particular skin property. Thus, it can be seen that the light source(s) 12 in the first light arrangement 10 preferably have a wide divergence (e.g. the light source(s) 12 emit light at the same or similar intensity across a wide angle (or even in all directions) and the light source(s) in the second light arrangement 14 should have a narrow or wide divergence, depending on the skin property to be measured. An example of a light source that can provide a narrow divergence (i.e. only emitting light across a narrow angle) is a laser-based light source or a light source with a lens arrangement to provide collimated light. Where a light arrangement is required to provide light that can have both wide and narrow divergence, e.g. in the case of the second light arrangement 14 in Table 1, the light arrangement can comprise multiple light sources that have different divergence properties (e.g. LEDs with different collimation angles, or light sources with different lens arrangements), and the appropriate light source(s) can be operated when a particular skin property is to be measured. The RGB detector channel refers to a capture mode of the image sensor 6. In particular, the image sensor 6 can be controlled to capture images in colour (i.e. RGB mode), or in one or more colour channels (i.e. in red (R), green (G) and/or blue (B) mode).

The skin parameter redness can be measured using the second light arrangement 14, with all light sources 16 being operated at the same time to evenly illuminate the skin sample 34. The redness can be determined based on the redness values of pixels in the acquired image (e.g. the value of the R component for each pixel). For example the redness can be determined as the average of the redness values for all of the pixels in the acquired image. A measure of colour contrast can also be used to determine the redness.

The skin parameter pores and/or blackheads (which can be considered as clogged or blocked pores) can be measured using the third light arrangement 18, with all light sources 20 being operated at the same time to evenly illuminate the skin sample 34. As light from this light arrangement 18 does not specularly reflect to the image sensor unit 4, pores and blackheads can be identified by differences in contrast in the acquired image. Image analysis (for example using a 'machine learning' trained algorithm) can be used to identify pores/blackheads and quantify their number and/or their size. Image analysis can also distinguish between pores and blackheads.

Figure 6:
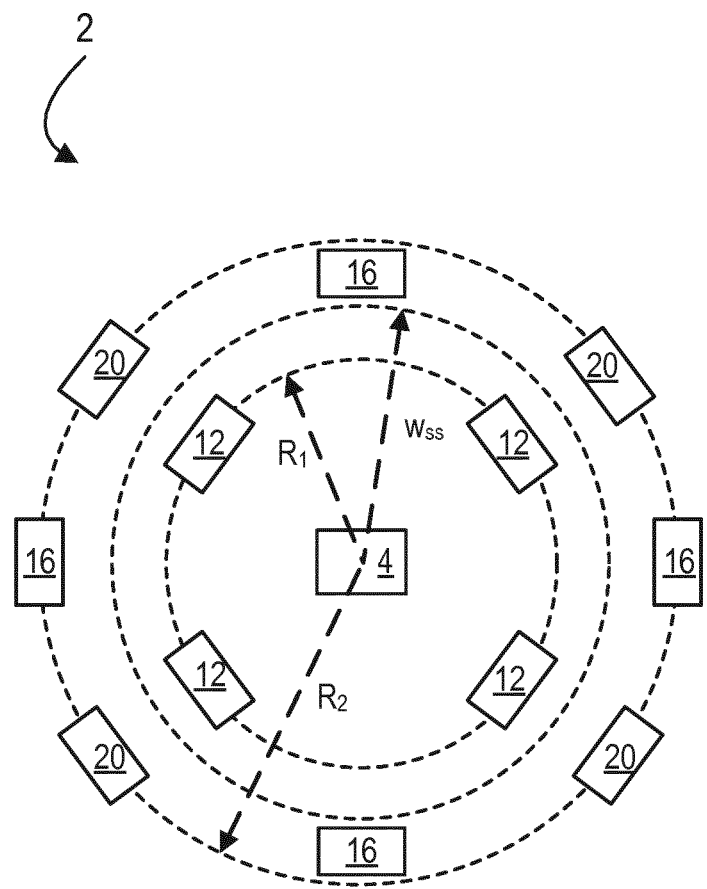
FIG. 6 is a front view of an apparatus showing another exemplary arrangement of light sources according to an embodiment.

FIG. 6 shows a front view of another exemplary apparatus 2. This apparatus 2 generally corresponds to the apparatus 2 shown in FIG. 5, although the light sources 16 in the second light arrangement 14 are in different positions with respect to the image sensor unit 4 (i.e. a different spatial distribution). In particular, the light sources 12, 20 for the first light arrangement 10 and the third light arrangement 18 are offset diagonally with respect to the orientation of the image sensor unit 4, but the light sources 16 for the second light arrangement 14 are offset vertically and horizontally with respect to the orientation of the image sensor unit 4. In addition, in this embodiment the light sources 16 for the second light arrangement 14 and the light sources 20 for the third light arrangement 18 are generally the same distance from the optical axis of the image sensor unit 4. Furthermore, as the image sensor 6 has a rectangular shape, with the vertical direction being shorter than the horizontal direction, the light sources 16 for the second light arrangement 14 offset vertically with respect to the image sensor unit 4 can be positioned closer to the optical axis of the image sensor unit 4 than the light sources 16 for the second light arrangement 14 that are offset horizontally with respect to the image sensor unit 4. This positioning can enable the apparatus 2 to be more compact.

Figure 7:
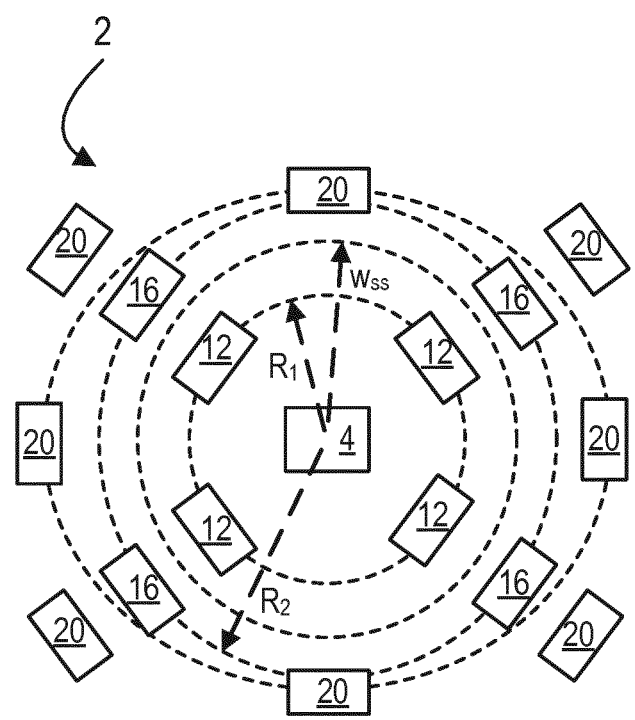
FIG. 7 is a front view of an apparatus showing another arrangement of light sources according to an embodiment.

FIG. 7 shows a front view of another exemplary apparatus 2. This apparatus 2 generally corresponds to the apparatus 2 shown in FIG. 5, although the third light arrangement 18 comprises eight light sources 20 arranged generally equidistant from a midpoint of the image sensor unit 4. The light sources 20 are vertically, horizontally and diagonally offset with respect to the orientation of the image sensor unit 4. In this embodiment the light sources 20 for the third light arrangement 18 are further from the image sensor unit 4 than the light sources 16 for the second light arrangement 14. This increase in the distance from the image sensor unit 4 provides a shallower angle of illumination and therefore a larger shadowing effect on the skin, making the structure (e.g. texture) more visible in an acquired image. In some embodiments, the light sources 20 in the third light arrangement 18 can be different types, for example four of the light sources 20 can emit visible light, and the other four light sources 20 can emit UV light (since the UV light can enable a higher resolution for the structure measurement).

Figure 8:
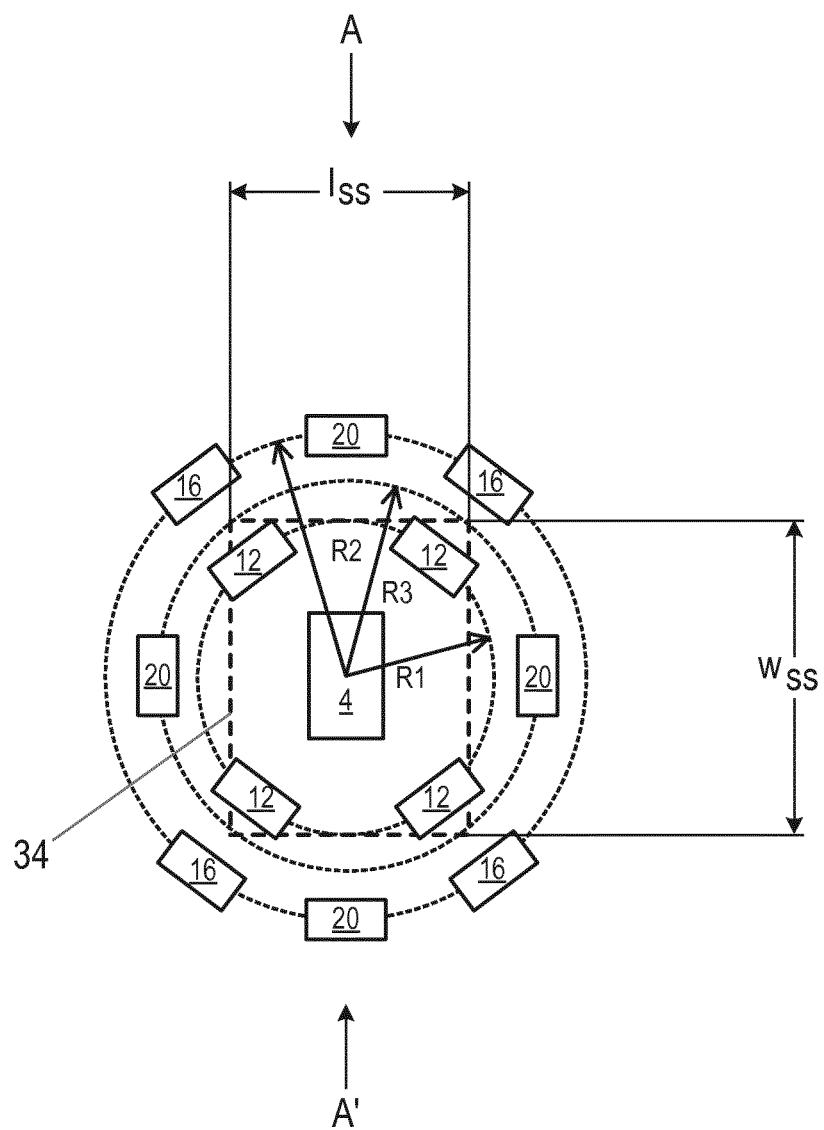
FIG. 8 is a front view of an apparatus according to another exemplary embodiment.
Figure 9:
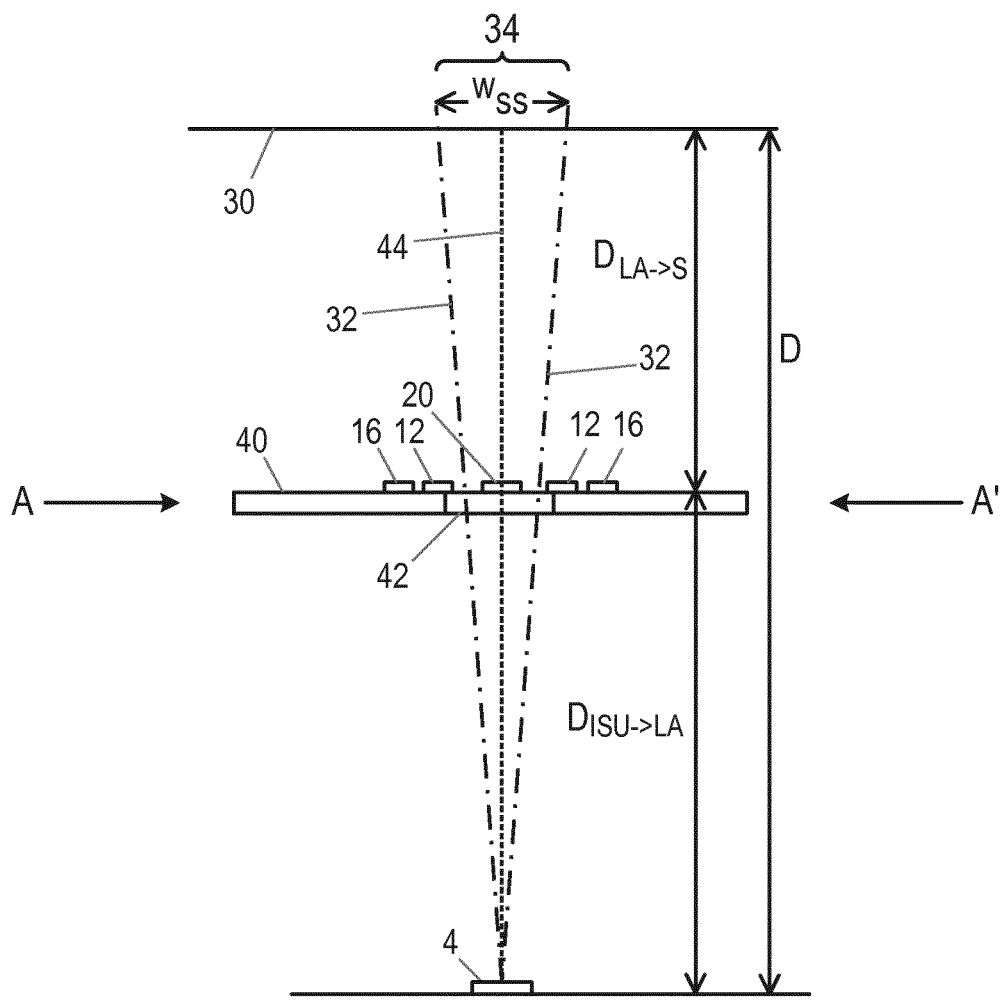
FIG. 9 shows a cross-section through the apparatus in FIG. 8.

FIG. 8 shows a front view of another exemplary apparatus 2, and FIG. 9 shows a cross-section through line A-A' in FIG. 8. This exemplary apparatus 2 includes first, second and third light arrangements 10, 14, 18. A first polariser is provided to polarise the light incident on the image sensor unit 4, and second polarisers are provided to polarise the light emitted by the light sources 16 in the second light arrangement 14. The second polarisers are crossed with respect to the first polariser as described above.

In this exemplary apparatus 2, the light arrangements 10, 14, 18 are arranged in a plane that is between the image sensor unit 4 and the skin 30. That is, the image sensor unit 4 is spaced the predetermined working distance D from the skin 30 as in the earlier embodiments, but the light arrangements 10, 14, 18 are positioned less than distance D to the skin 30. The distance between the light arrangements 10, 14, 18 and the skin is denoted $D_{LA->S}$ and the distance between the image sensor unit and the light arrangements 10, 14, 18 is denoted $D_{ISU->LA}$. By positioning the light arrangements closer to the skin 30 than the image sensor unit 4, the apparatus 2 can be made more compact, as the light sources can be closer to the optical axis of the image sensor unit 4 while achieving the specular or non-specular illumination of the skin sample as appropriate for the particular light arrangement. In this exemplary apparatus 2, the light sources for the light arrangements 10, 14, 18 are disposed on a circuit board 40, and the circuit board 40 has an aperture or hole 42 through which the image sensor unit 4 is able to view the skin sample 34. The light sources of the light arrangements 10, 14, 18 are arranged around the aperture 42. In this exemplary apparatus 2, the field of view of the image sensor unit 4 (as represented by lines 32) is such that it is narrower than the aperture 42, but in other embodiments, the aperture 42 could help define the size of the skin sample visible to the image sensor unit 4 through the aperture 42.

FIG. 8 shows the apparatus 2 from the point of view of the skin sample 34. FIG. 8 also shows an exemplary outline of the skin sample 34, which has width $w_{ss}$ and length $l_{ss}$. In FIG. 8 each of the first light arrangement 10, the second light arrangement 14 and the third light arrangement 18 comprise four light sources 12, 16, 20 that are arranged in respective rings around the image sensor unit 4, with the light sources 12, 16 each being offset diagonally with respect to the image sensor unit 4. The light sources 20 of the third light arrangement 18 are offset vertically and horizontally with respect to the orientation of the image sensor unit 4. Thus the light sources 12, 16, 20 in each ring are spatially distributed around the optical axis of the image sensor unit 4, so that the skin 30 is illuminated from different directions. The optical axis of the image sensor unit 4 is illustrated by line 44 in FIG. 9. The light sources 12, 16 in each ring are generally evenly spaced with respect to each other around the image sensor unit 4, although other configurations/spatial distributions are possible.

The light sources 12 in the first light arrangement 10 are each spaced from the image sensor unit 4 (and specifically spaced from the optical axis of the image sensor unit 4) by a distance $R_1$ so that specular reflections of the light on the skin sample are incident on the image sensor unit 4. The light sources 16 in the second light arrangement 14 and two of the light sources 20 of the third light arrangement 18 are each spaced from the image sensor unit 4 (and specifically spaced from the optical axis of the image sensor unit 4) by a distance $R_2$. $R_2$ is greater than $R_1$ so that specular reflections on the skin sample of the light from these light sources is not incident on the image sensor unit 4. The other two light sources 20 in the third light arrangement 18 are spaced from the optical axis of the image sensor unit 4 by a distance $R_3$, which in this embodiment is between $R_1$ and $R_3$, so that specular reflections on the skin sample of the light from these light sources is not incident on the image sensor unit 4. In alternative implementations, all of the light sources 16, 20 of the second and third light arrangements 14, 18 can be spaced the same distance from the optical axis of the image sensor unit 4.

In particular embodiments, $D_{LA->S}$ is 24 mm, or another distance in the range 20-60 mm, and $D_{ISU->LA}$ is 34 mm or 34.7 mm, or another distance in the range of 10-40 mm. In these embodiments, the predetermined working distance D can be 58 mm or 58.7 mm, or another distance in the range 30-100 mm. The field of view of the image sensor unit 4 can be such that, at a distance 58.7 mm from the skin 30, the skin sample 34 has width $w_{ss}$=11.45 mm (or about 11.5 mm or about 11 mm) and length $l_{ss}$=8.6 mm (or about 9 mm). The distance $R_1$ can be 5.5 mm, or another distance in the range 1-6 mm. The distance $R_2$ can be 8.75 mm or about 9 mm. The distance $R_3$ can be 7 mm. Alternatively, $R_2$ and/or $R_3$ can be any distance greater than 7 mm.

With the exemplary apparatus 2 shown in FIG. 8 (and the exemplary apparatuses 2 shown in FIGS. 5-7), the first light arrangement 10 can be used to obtain images that are processed to determine a value for the oiliness, shine and/or texture of the skin sample 34, the second light arrangement 14 can be used to obtain one or more images that are processed to determine a value for the redness, spots (identified by their colour), colour and/or pigmentation of the skin sample 34, and the third light arrangement 18 can be used to obtain one or more images that are processed to determine a value for the pores and blackheads of the skin sample 34.

Figure 10:
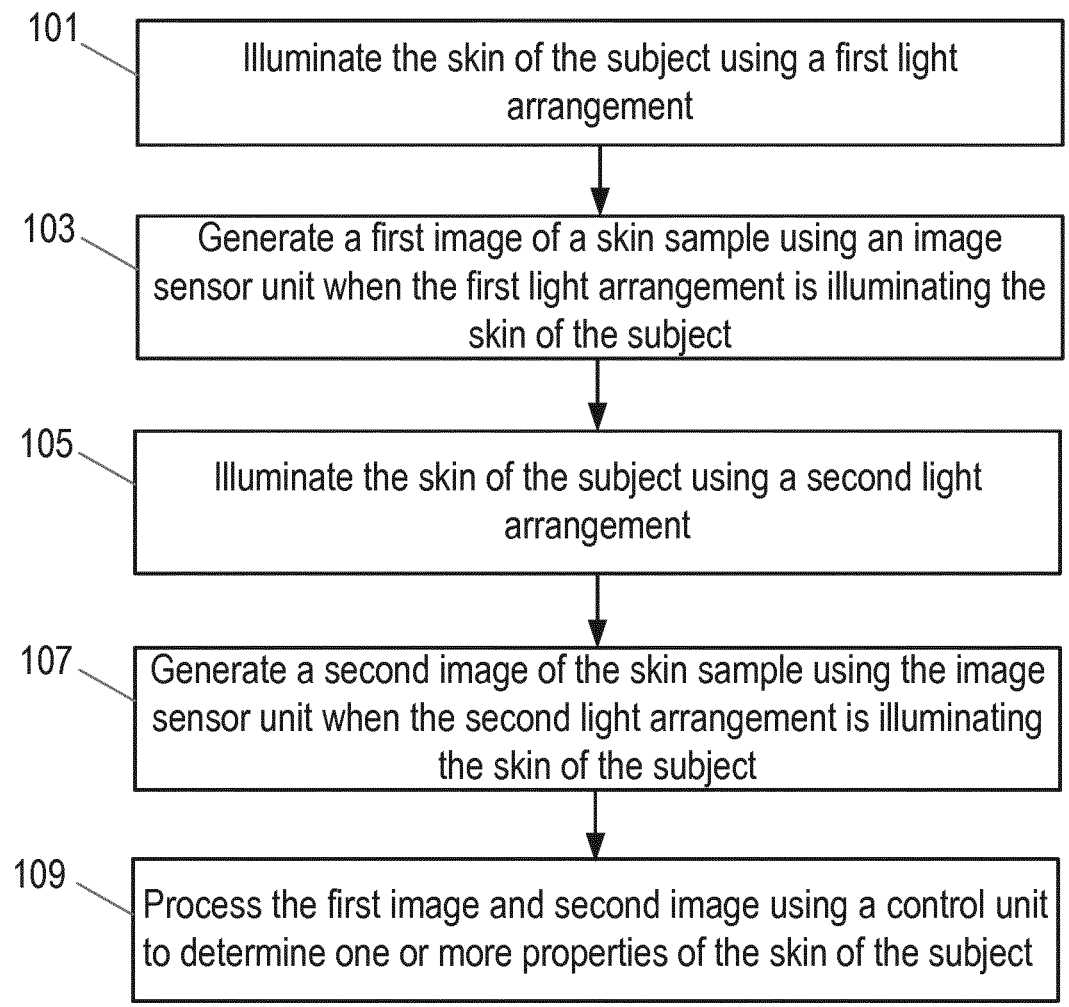
FIG. 10 is a flow chart illustrating a method according to an exemplary aspect.

A method of operating the system 1 to determine one or more properties of the skin 30 of a subject is illustrated in FIG. 10. As noted below, various steps of the method can be performed by the control unit 3 in conjunction with the image sensor unit 4, the first light arrangement 10 and the second light arrangement 14, and, where present, the third light arrangement 18.

In step 101, the skin of the subject is illuminated using the first light arrangement 10. This step can comprise the control unit 3 controlling the light source(s) 12 in the first light arrangement 10 to emit light. In embodiments where the first light arrangement 10 comprises multiple light sources 12, this step can comprise the skin being illuminated by all of the light sources 12 at once, or the skin being selectively illuminated by the light sources 12 one at a time.

In step 103, a first image of a skin sample 34 is generated using the image sensor unit 4. The first image is generated while the first light arrangement 10 is illuminating the skin 30. As described above, the skin sample 34 corresponds to an area of the skin 30 that is within the FOV of the image sensor unit 4 when the skin 30 is spaced a predetermined working distance D from the image sensor unit 4.

In step 105, the skin of the subject is illuminated using the second light arrangement 14. This step can comprise the control unit 3 controlling the light source(s) 16 in the second light arrangement 14 to emit light. In embodiments where the second light arrangement 14 comprises multiple light sources 16, this step can comprise the skin being illuminated by all of the light sources 16 at once, or the skin being illuminated by the light sources 16 one at a time.

In step 107, a second image of skin sample 34 is generated using the image sensor unit 4. The second image is generated while the second light arrangement 14 is illuminating the skin 30.

Next, in step 109, the first image and the second image are processed by the control unit 3 to determine one or more properties of the skin of the subject. As noted above, the skin property to be determined depends on the light arrangement used to illuminate the skin sample 34.

Techniques for determining the various skin properties mentioned above from images of a skin sample 34 are known to those skilled in the art, and therefore further details are not provided herein.

In particular embodiments of the method, the method is for determining values of multiple skin properties, with a first skin property being determined from images obtained when the skin sample is illuminated with light from the first light arrangement 10 and a second skin property being determined from images obtained when the skin sample is illuminated with light from the second light arrangement 14. The first light arrangement 10 comprises multiple light sources 12 and the control unit 3 controls the light sources 12 to illuminate the skin sample individually (i.e. one at a time), and the image sensor unit 4 obtains a respective image when each of the light sources 12 is active. These images are referred to as 'first' images. The second light arrangement 14 includes one or more light sources 16, and the image sensor unit 4 obtains one or more images when the light source or light sources 16 are active together. This or these images are referred to as 'second' images.

To determine a value for the first skin property (e.g. oiliness, shine, gloss or texture), the control unit 3 processes each first image to determine a respective initial value for the first skin property, and then combines the determined initial values to determine a value for the first skin property. The combination can be an average, e.g. mean, mode or median. To determine a value for the second skin property (e.g. colour, redness, pigmentation, texture, pores, blackheads, etc.), the control unit 3 processes the one or more second images to determine a value for the second skin property.

In embodiments where the apparatus 2 comprises a third light arrangement 18, the control unit 3 can selectively control the third light arrangement 18 to illuminate the skin sample 34 when a third skin property is to be determined (e.g. pores or blackheads). Where the third light arrangement 18 comprises multiple light sources 20, the control unit 3 can control the light sources 20 to illuminate the skin sample 34 at the same time. The image sensor unit 4 obtains one or more images when the light sources 20 are active. This or these images are referred to as 'third' images. The control unit 3 processes the third image(s) to determine values for the third skin property.

In embodiment where the apparatus 2 also comprises an impedance sensor for measuring impedance of the skin of the subject, the control unit 3 can control the impedance sensor to measure impedance, and process the impedance measurements to determine a measure of the hydration level of the skin.

There is therefore provided an improved system, apparatus and method for obtaining images for use in determining properties of skin of a subject. In general, the first light arrangement 10 enables skin properties to be measured that require specular reflection in the image (e.g. oiliness, shine, gloss, texture), the second light arrangement 14, with cross-polarisation with the image sensor unit 4, enables skin properties relating to colour to be measured without specular disturbances (e.g. colour, colour variety, pigmentation, presence of hair), and the third light arrangement 18 enables skin properties relating to the skin structure to be measured without specular disturbances (e.g. pores, blackheads).

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system for determining values of a plurality of properties of skin of a subject, the system comprising:
    a control unit; and
    an apparatus for obtaining images for use in determining the values of the plurality of properties of skin of the subject, the apparatus comprising:

an image sensor unit for generating an image of a skin sample, wherein the skin sample corresponds to an area of skin of the subject within a field of view, FOV, of the image sensor unit when the skin of the subject is spaced a predetermined working distance from the image sensor unit;

a first light arrangement comprising a plurality of light sources that are spatially distributed around an optical axis of the image sensor unit for illuminating the skin of the subject from a respective plurality of directions;

a second light arrangement comprising one or more light sources for illuminating the skin of the subject; and wherein the plurality of light sources in the first light arrangement are spaced from the optical axis of the image sensor unit and arranged such that light emitted by the light sources in the first light arrangement that is specularly reflected by a skin sample at the predetermined working distance is incident on the image sensor unit;

wherein the one or more light sources in the second light arrangement are spaced from the optical axis of the image sensor unit and arranged such that light emitted by the light sources in the second light arrangement that is specularly reflected by a skin sample at the predetermined working distance is not incident on the image sensor unit;

wherein the control unit is configured to:

selectively and individually control each of the light sources in the first light arrangement to individually illuminate the skin of the subject;

receive a respective plurality of first images from the image sensor unit, each first image being obtained by the image sensor unit when a respective light source in the first light arrangement is illuminating the skin;

process each first image to determine a respective initial value for a first skin property and combine the determined initial values to determine a value for the first skin property;

selectively control the second light arrangement to illuminate the skin of the subject;

receive one or more second images generated by the image sensor unit, each second image being obtained by the image sensor unit when the second light arrangement is illuminating the skin of the subject; and process the one or more received second images to determine a value for one or more second skin properties.

2. The system as claimed in claim 1, wherein the plurality of light sources in the first light arrangement and the one or more light sources in the second light arrangement are arranged in a plane.

3. The system as claimed in claim 1, wherein the plurality of light sources in the first light arrangement and the one or more light sources in the second light arrangement are spaced from the skin of the subject by less than the predetermined working distance.

4. The system as claimed in claim 1, wherein the first light arrangement comprises at least three light sources arranged generally equidistant from the optical axis of the image sensor unit.

5. The system as claimed in claim 1, wherein the second light arrangement comprises a plurality of light sources.

6. The system as claimed in claim 5, wherein the control unit is configured to selectively control the plurality of light sources in the second light arrangement to illuminate the skin of the subject at the same time.

7. The system as claimed in claim 1, wherein the second light arrangement comprises at least three light sources arranged generally equidistant from the optical axis of the image sensor unit.

8. The system as claimed in claim 1, wherein the first skin property is one of oiliness, gloss and skin texture.

9. The system as claimed in claim 8, wherein the first skin property is oiliness, and the control unit is configured to process each first image to determine a respective initial value for oiliness based on one or more parameters including an amount of specular reflection from the skin sample, a distribution, granularity and/or intensity of specular reflection from the skin sample, a roughness or texture of the skin, principal component analysis of the image, a histogram shape encoding of texture maps and contrast in the image.

10. The system as claimed in claim 1, wherein the second skin property is one of skin texture, colour, redness, pigmentation, pores, presence of spots and presence of hairs.

11. The system as claimed in claim 1, wherein the apparatus further comprises:

a first polarising filter arranged with respect to the image sensor unit such that the polarising filter polarises light incident on the image sensor unit.

12. The system as claimed in claim 11, wherein the apparatus further comprises:

a respective second polarising filter for each light source in the second light arrangement that is for polarising the light emitted by the light source in the second light arrangement, wherein a polarising direction of the second polarising filter is orthogonal to a polarising direction of the first polarising filter.

13. The system as claimed in any of claim 12, wherein the second skin property is one of colour, redness, spots and pigmentation.

14. The system as claimed in claim 12, wherein the apparatus further comprises:

a third light arrangement comprising one or more light sources for illuminating the skin of the subject;

wherein the one or more light sources in the third light arrangement are spaced from the optical axis of the image sensor unit and arranged such that light emitted by the light sources in the third light arrangement that is specularly reflected by a skin sample at the predetermined working distance is not incident on the image sensor unit;

wherein the control unit is further configured to:

selectively control the third light arrangement to illuminate the skin of the subject;

receive one or more third images generated by the image sensor unit, each third image being obtained by the image sensor unit when the third light arrangement is illuminating the skin of the subject; and process the one or more received third images to determine values for one or more third skin properties.

15. The system as claimed in claim 14, wherein the third light arrangement comprises a plurality of light sources.

16. The system as claimed in claim 15, wherein the control unit is configured to selectively control the plurality of light sources in the third light arrangement to illuminate the skin of the subject at the same time.

17. The system as claimed in claim 14 wherein the third light arrangement comprises at least three light sources arranged generally equidistant from the optical axis of the image sensor unit.

18. The system as claimed in claim 14, wherein the third skin property is one of pores and blackheads.

19. The system as claimed in claim 1, wherein the apparatus further comprises an impedance sensor for measuring an impedance of the skin of the subject; and wherein the control unit is further configured to receive impedance measurements from the impedance sensor, and to process the received impedance measurements to determine a hydration level of the skin.

20. A system as claimed in claim 1, wherein the control unit is configured to combine the determined initial values to determine the value for the first skin property by averaging the determined initial values to determine the value for the first skin property.

21. Method of determining values of a plurality of properties of skin of a subject, the method comprising:

illuminating the skin of the subject using a first light arrangement comprising a plurality of light sources, wherein the skin of the subject is illuminated selectively and individually by each of the plurality of light sources;

generating a respective first image of a skin sample using an image sensor unit when each of the light sources in the first light arrangement is illuminating the skin of the subject, wherein the skin sample corresponds to an area of skin of the subject within a field of view, FOV, of the image sensor unit when the skin of the subject is spaced a predetermined working distance from the image sensor unit;

illuminating the skin of the subject using a second light arrangement comprising one or more light sources;

generating one or more second images of the skin sample using the image sensor unit when the second light arrangement is illuminating the skin of the subject;

processing, using a control unit, each first image to determine a respective initial value for a first skin property and combining the determined initial values to determine a value for a first skin property; and processing, using the control unit, the one or more second images to determine a value for one or more second skin properties;

wherein the plurality of light sources in the first light arrangement are spatially distributed around an optical axis of the image sensor unit to illuminate the skin of the subject from a plurality of directions, and the plurality of light sources are arranged such that light emitted by the light sources in the first light arrangement that is specularly reflected by a skin sample at the predetermined working distance is incident on the image sensor unit;

wherein the one or more light sources in the second light arrangement are spaced from the optical axis of the image sensor unit and arranged such that light emitted by the light sources in the second light arrangement that is specularly reflected by a skin sample at the predetermined working distance is not incident on the image sensor unit.

22. The method as claimed in claim 21, wherein combining the determined initial values to determine a value for a first skin property comprises averaging the determined initial values to determine the value for the first skin property.

\* \* \* \* \*